(12) United States Patent
Bell et al.

(10) Patent No.: US 11,244,744 B2
(45) Date of Patent: Feb. 8, 2022

(54) RISK EVALUATION AND MANAGEMENT STRATEGY INVOLVING PATIENT FOLLOW-UPS RELATING TO THE USE OR DISCONTINUATION OF A COMPLEMENT INHIBITOR

(71) Applicant: Alexion Pharmaceuticals, Inc., Boston, MA (US)

(72) Inventors: Leonard Bell, Woodbridge, CT (US); Camille Bedrosian, Woodbridge, CT (US)

(73) Assignee: Alexion Pharmaceuticals, Inc., Boston, MA (US)

( * ) Notice: Subject to any disclaimer, the term of this patent is extended or adjusted under 35 U.S.C. 154(b) by 301 days.

(21) Appl. No.: 15/614,964

(22) Filed: Jun. 6, 2017

(65) Prior Publication Data
US 2017/0277835 A1  Sep. 28, 2017

Related U.S. Application Data

(62) Division of application No. 14/941,080, filed on Nov. 13, 2015, now Pat. No. 11,031,102.

(60) Provisional application No. 62/208,027, filed on Aug. 21, 2015, provisional application No. 62/185,149, filed on Jun. 26, 2015, provisional application No. 62/080,805, filed on Nov. 17, 2014.

(51) Int. Cl.
| | | |
|---|---|---|
| *G01N 33/48* | (2006.01) | |
| *G16H 10/20* | (2018.01) | |
| *G16H 10/60* | (2018.01) | |
| *G16H 15/00* | (2018.01) | |
| *G16H 20/10* | (2018.01) | |
| *G06G 7/58* | (2006.01) | |
| *G16H 40/67* | (2018.01) | |

(52) U.S. Cl.
CPC ............. *G16H 10/20* (2018.01); *G16H 10/60* (2018.01); *G16H 15/00* (2018.01); *G16H 20/10* (2018.01); *G16H 40/67* (2018.01); *Y02A 90/10* (2018.01)

(58) Field of Classification Search
None
See application file for complete search history.

(56) References Cited

U.S. PATENT DOCUMENTS

| | | |
|---|---|---|
| 7,919,094 B2 | 4/2011 | Schwaeble et al. |
| 7,999,081 B2 | 8/2011 | Tedesco et al. |
| 8,241,628 B2 | 8/2012 | Diefenbach-Streiber et al. |
| 8,563,006 B2 | 10/2013 | Zlotnick et al. |
| 8,883,158 B2 | 11/2014 | Diefenbach-Streiber et al. |
| 2009/0299767 A1 | 12/2009 | Michon et al. |
| 2010/0034809 A1 | 2/2010 | Diefenbach-Streiber et al. |
| 2010/0166748 A1 | 7/2010 | Guild et al. |
| 2013/0246083 A1 | 9/2013 | Bell |
| 2013/0291060 A1 | 10/2013 | Moore |

FOREIGN PATENT DOCUMENTS

WO     2010054403 A1     5/2010

OTHER PUBLICATIONS

Appel, G. et al., J Am Soc Nephrol, vol. 16, pp. 1392-1404 (2005).
Frei, Y. et al., Molecular and Cellular Probes, vol. 1, pp. 141-149 (1987).
Holers, V. et al., Molecular Immunology, vol. 41, pp. 147-152 (2004).
Holers, V., Immunological Reviews, vol. 223, pp. 300-316 (2008).
International Search Report and Written Opinion, PCT/ US2015/60677, dated Feb. 4, 2016, 11 pages.
Keefe, A. et al., Nature Reviews Drug Discovery, vol. 9, pp. 537-550 (2010).
Molines, T. et al., Molecular Immunology, vol. 43, pp. 107-121 (2006).
Romay-Penabad, et al., Lupus, vol. 23, pp. 1324-1326 (2014).
Soliris Prescribing Information, 6 pages, Apr. 2014.
Wurzner, R et al., Complement Inflamm, vol. 8, pp. 328-340 (1991).
International Preliminary Report on Patentability, PCT/US2015/60677, dated May 23, 2017, 7 pages.
U.S. Appl. No. 14/941,080, filed Nov. 13, 2015, Leonard Bell.
U.S. Appl. No. 14/941,080, May 18, 2017.

*Primary Examiner* — Eric S Dejong
(74) *Attorney, Agent, or Firm* — Nelson Mullins Riley & Scarborough LLP

(57) ABSTRACT

This invention provides, inter alia, a complement-inhibitor-based treatment plan coupled with a risk evaluation and management strategy ("REMS") and a safety support program ("SSP") for reinforcing the REMS. The REMS and SPP are implemented using one or more computer devices with software tools programmed to enforce conditions of the REMS and/or prompt follow-ups by registered nurses enrolled in the SSP. The software tool(s) determines whether a prescriber requesting the complement inhibitor has agreed to abide by the REMS, and can prompt a provider of the complement inhibitor to provide updated educational materials to the prescriber at predetermined times or intervals, to monitor the prescriber for compliance with the REMS, and/or to monitor patients for signs of adverse events. Using exemplary embodiments described herein, a risk of adverse events (especially, but not limited to, meningococcal infections) can be managed and an incidence of the adverse events can be reduced.

11 Claims, 14 Drawing Sheets

| PATIENT ID | REPRESENTATIVE ID | AGE | GENDER | REGISTERED? | DATE OF BEGINNING OF DRUG ADMINISTRATION | DATE OF DRUG DISCONTINUATION |
|---|---|---|---|---|---|---|
| 1254 | 980 | 46 | M | Y | OCT 1, 2011 | FEB 24, 2012 |
| 574 | 854 | 28 | F | Y | MAY 3, 2005 | N/A |
| 387 | N/A | 62 | F | N | N/A | N/A |
| 1345 | 1345 | 58 | M | Y | DEC 12, 2008 | JUL 23, 2008 |

RISK EVALUATION AND MANAGEMENT STRATEGY INVOLVING PATIENT FOLLOW-UPS RELATING TO THE USE OR DISCONTINUATION OF A COMPLEMENT INHIBITOR

RELATED APPLICATIONS

This application is a Divisional Application of U.S. patent application Ser. No. 14/941,080 filed Nov. 13, 2015, which claims priority to U.S. provisional patent application Ser. No. 62/080,805, filed Nov. 17, 2014, U.S. provisional patent application Ser. No. 62/185,149, filed Jun. 26, 2015, and U.S. provisional patent application Ser. No. 62/208,027, filed Aug. 21, 2015, the contents of which are hereby incorporated by reference.

TECHNICAL FIELD

This invention relates to the fields of immunology and infectious disease.

BACKGROUND OF THE INVENTION

Complement is an essential component of the immune system and is of substantial relevance for the destruction of invading microorganisms and for maintaining tissue homeostasis, including the protection against autoimmune diseases. Excessive or uncontrolled complement activation, however, significantly contributes to undesired tissue damage. Complement activation presents a considerable risk of harming the host by directly and indirectly mediating inflammatory tissue destruction. Complement plays a prominent role of in the pathogenesis of numerous inflammatory diseases.

In recent years, great progress has been made in inhibiting complement activation for potential therapies for complement-relevant diseases. A certain degree of inhibition of complement activation may be sufficient to reduce its detrimental effects but still preserve the defense mechanisms against invading pathogens. The redundancy of the three complement activation pathways may reduce the risk of infection if only one pathway is selectively blocked. In addition, the risk of infectious complications is most probably highest when blocking the comparatively upstream complement component C3. Some complement inhibitors, including antibodies or antigen-binding fragments specifically recognizing and antagonizing the downstream complement component C5, e.g., eculizumab (Soliris®), have been shown effective in treatment of various diseases.

In some situations, the use and/or discontinuation of a complement inhibitor can lead to an increased risk for adverse events, such as meningococcal infections, general infections, and hemolysis.

SUMMARY OF THE INVENTION

The present invention provides a solution to the issues discussed above by providing systems, methods, and mediums for supporting a complement-inhibitor-based treatment plan. According to certain embodiments of the invention, the complement-inhibitor-based treatment plan may be combined with a novel regimen of pre-treatment, intra-treatment, and/or post-treatment follow ups with prescribers and patients. In practice, this regimen decreases the incidence of adverse events associated with complement-inhibitor based treatments.

In certain aspects, a method is provided comprising receiving a request from a prescriber to distribute a complement inhibitor and verifying that the prescriber has agreed to the following conditions: (a) to vaccinate patients with a *Neisseria* meningococcal type B specific vaccine, and/or revaccinate patients according to a pre-determined schedule with a *Neisseria* meningococcal type B specific vaccine at predetermined times or intervals, (b) to provide the patients with educational materials regarding the complement inhibitor, and (c) that the prescriber has reviewed information relating to administering the complement inhibitor. The claimed method further recites accessing, using a computer with a processor programmed to perform the accessing, a database of certified prescribers, and adding, using the processor, the prescriber to the database. The adding to the database is only performed if the prescriber has agreed to conditions (a)-(c).

The claimed method further requires receiving a requisition from the prescriber, the requisition requesting that the prescriber be provided with the complement inhibitor, inspecting using the processor the database of certified prescribers, and authorizing the prescriber to receive the complement inhibitor only if the prescriber is in the database of certified prescribers.

In certain aspects, a method is provided for treating a patient in need of treatment with a complement inhibitor, or inhibiting formation of terminal complement in a patient, comprising administering an effective amount of a complement inhibitor to the patient who has been prescribed the complement inhibitor by a certified prescriber of the complement inhibitor, where a prescriber becomes a certified prescriber of the complement inhibitor by first requesting the provider over a network, which is part of a system comprising a computer with a processor, to become authorized to prescribe the complement inhibitor, and the provider then verifies that the prescriber has agreed to the following conditions:

(a) to vaccinate and/or revaccinate patients receiving the the complement inhibitor, at predetermined times or intervals, with one or more meningococcal vaccines, including a *Neisseria* meningococcal type B specific vaccine;

(b) to provide patients with educational materials regarding the complement inhibitor, and (c) that the prescriber has reviewed information provided by the provider relating to the complement inhibitor.

Once verified, adding, using the processor, the prescriber to the database as a certified prescriber; then using the processor to generate a prescription approval code and authorizing, using the processor, the prescriber to prescribe to a patient the complement inhibitor.

In certain other aspects, a system is provided for a provider of a complement inhibitor, such as eculizumab or an eculizumab variant, to communicate over a network with a prescriber of the complement inhibitor to authorize the prescriber to prescribe a complement inhibitor to a patient in need thereof. The system comprises a computer device. The computer devices includes a processor and a database of the certified prescribers of a complement inhibitor. A prescriber becomes a certified prescriber of the complement inhibitor by first requesting the provider to become authorized to prescribe the complement inhibitor. Then the prescriber is verified by the provider to be a prescriber that has agreed to the following conditions: (a) to vaccinate and/or revaccinate patients receiving the complement inhibitor, at predetermined times or intervals, with one or more meningococcal vaccines, including a meningococcal vaccine to *Neisseria*

*meningitidis* serogroup B; (b) to provide patients with educational materials regarding the complement inhibitor, and (c) that the prescriber has reviewed information provided by the provider relating to the complement inhibitor. Once verified, the processor adds the prescriber to the database as a certified prescriber. The processor of the computer device can then generate a prescription approval code based on a comparison of an on-line transmission of a prescriber requesting that the prescriber be able to prescribe to a patient the complement inhibitor, with the database of certified prescribers, and after using the processor to inspect the database of certified prescribers and to ascertain that the prescriber is a certified prescriber, authorize, using the processor, the prescriber to prescribe to a patient the complement inhibitor. The computer device also comprises an interface configured to send an on-line transmission to the prescriber the prescription approval code.

In yet other aspects, a non-transitory computer-readable storage medium is provided, the medium storing instructions that, when executed by a processor of a computer device, cause the processor to: (A) receive verification that a prescriber requesting to administer a complement inhibitor, such as eculizumab or an eculizumab variant, has agreed to the following conditions: (a) to vaccinate and/or revaccinate patients receiving the complement inhibitor, at predetermined times or intervals, with one or more meningococcal vaccines, including a meningococcal vaccine to *Neisseria meningitidis* serogroup B; (b) to provide patients with educational materials regarding eculizumab or an eculizumab variant, and (c) that the prescriber has reviewed information relating to administering the complement inhibitor; and (B) access a database of certified prescribers; and add the prescriber to the database. The storage medium includes instructions that also (C) inspect the database of certified prescribers in response to a requisition from the prescriber requesting that the prescriber be provided with eculizumab or an eculizumab variant; and (D) authorizing the prescriber to prescribe eculizumab or an eculizumab variant only if the prescriber is in the database of certified prescribers.

In yet other aspects, a method is provided, comprising: receiving a request from a patient enrolled in treatment plan of a complement inhibitor, such as eculizumab or an eculizumab variant, to be enrolled in a safety support program; adding, using a computer device with a processor suitably programmed to perform the adding, the patient to a patient safety registry; and prompting, using the processor, an authorized user to follow up with the patient to discuss the possibility of adverse events associated with the complement inhibitor, the prompting instructing the authorized user to discuss:

(a) symptoms of the adverse events, and
(b) whether the patient has experienced an unreported adverse event, the prompting performed at one or more predetermined times or intervals.

Numerous other aspects are provided in accordance with these and other aspects of the disclosure. Other features and aspects of the present disclosure will become more fully apparent from the following drawings, detailed description, and the appended claims.

BRIEF DESCRIPTION OF THE DRAWINGS

FIG. 2 depicts an exemplary data structure for storing records in a patient database.

DETAILED DESCRIPTION

Figure 1A:
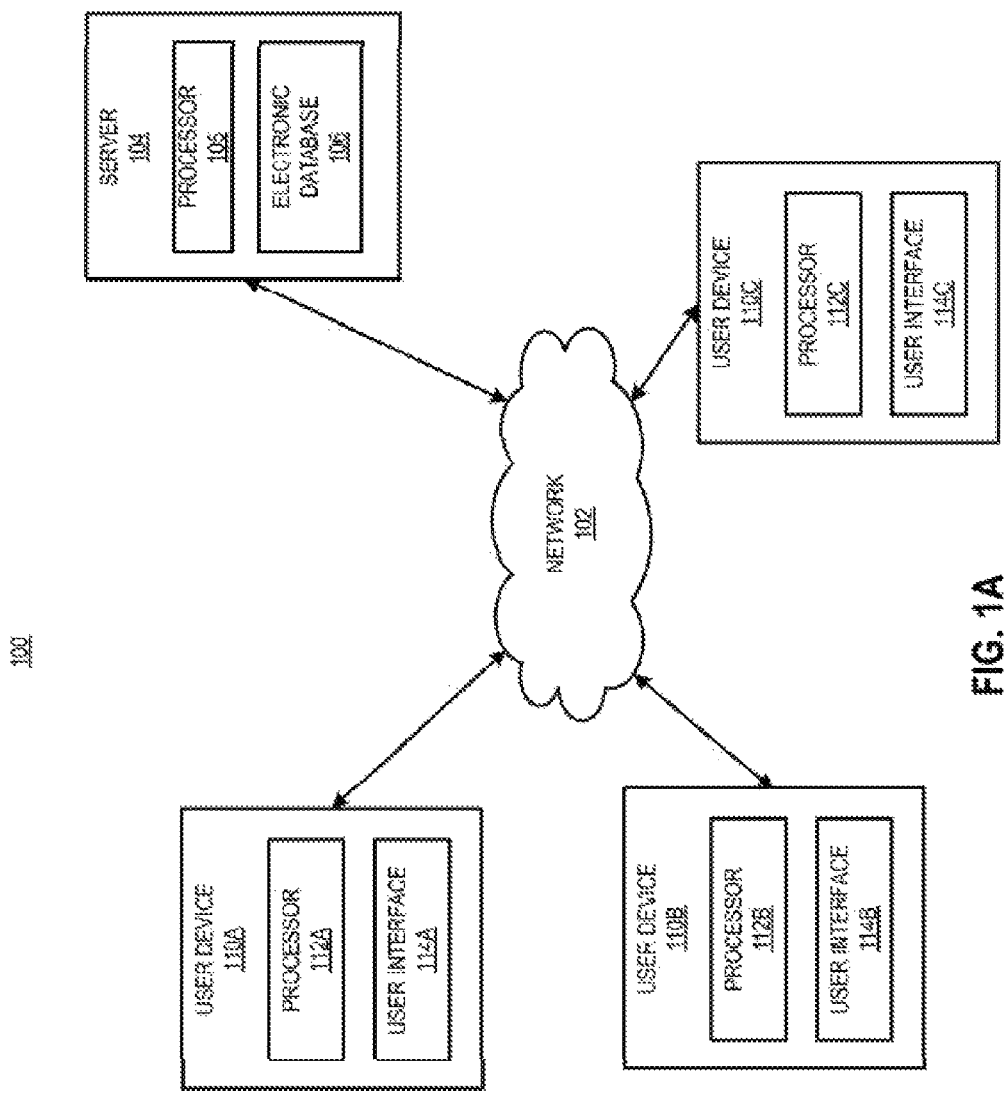
FIG. 1A and FIG. 1B depict exemplary network-based embodiments for administering a complement-inhibitor-based treatment plan.

In certain aspects, a method is provided, comprising receiving a request from a prescriber to distribute a complement inhibitor; verifying that the prescriber has agreed to the following conditions: (a) to vaccinate patients with a *Neisseria* meningococcal type B specific vaccine, and/or revaccinate patients according to a pre-determined schedule with a *Neisseria* meningococcal type B specific vaccine at pre-determined times or intervals, (b) to provide the patients with educational materials regarding the complement inhibitor, and (c) that the prescriber has reviewed information relating to administering the complement inhibitor. The method also includes accessing, using a computer with a processor programmed to perform the accessing, a database of certified prescribers; and adding, using the processor, the prescriber to the database, the adding performed only if the prescriber has agreed to conditions (a)-(c); receiving a requisition from the prescriber, the requisition requesting that the prescriber be provided with the complement inhibitor; inspecting, using the processor, the database of certified prescribers; and authorizing, using the processor, the prescriber to receive the complement inhibitor only if the prescriber is in the database of certified prescribers.

In certain aspects, a method is provided of treating a patient in need of treatment with a complement inhibitor, or inhibiting formation of a terminal complement in a patient, comprising administering an effective amount of a complement inhibitor to the patient who has been prescribed the complement inhibitor by a certified prescriber of the complement inhibitor; wherein a prescriber becomes a certified prescriber of the complement inhibitor by: first requesting the provider over a network, which is part of a system comprising a computer with a processor, to become authorized to prescribe the complement inhibitor; the provider then verifying that the prescriber has agreed to the following conditions: (a) to vaccinate and/or revaccinate patients receiving the the complement inhibitor, at predetermined times or intervals, with one or more meningococcal vaccines, including a *Neisseria* meningococcal type B specific vaccine; (b) to provide patients with educational materials regarding the complement inhibitor, and (c) that the prescriber has reviewed information provided by the provider relating to the complement inhibitor. Once verified, adding, using the processor, the prescriber to the database as a certified prescriber; then using the processor to generate a prescription approval code and authorizing, using the processor, the prescriber to prescribe to a patient the complement inhibitor.

In certain other aspects, a system is provided for a provider of a complement inhibitor, such as eculizumab or an eculizumab variant, to communicate over a network with a prescriber of the complement inhibitor to authorize the prescriber to prescribe a complement inhibitor to a patient in need thereof. The system comprises a computer device. The computer device comprises a processor comprising a database of the certified prescribers of a complement inhibitor. A prescriber becomes a certified prescriber of the complement inhibitor by first requesting the provider to become authorized to prescribe the complement inhibitor. Then the prescriber is verified by the provider to be a prescriber that has agreed to the following conditions: (a) to vaccinate and/or revaccinate patients receiving the complement inhibitor, at predetermined times or intervals, with one or more meningococcal vaccines, including a meningococcal vaccine to *Neisseria meningitidis* serogroup B; (b) to provide patients with educational materials regarding the complement inhibitor, and (c) that the prescriber has reviewed information provided by the provider relating to the complement inhibitor. Once verified, the processor adds the prescriber to the database as a certified prescriber. The processor can then generate a prescription approval code based on comparison of an on-line transmission of a prescriber requesting that the prescriber be able to prescribe to a patient the complement inhibitor, with the database of certified prescribers. After using the processor to inspect the database of certified prescribers and to ascertain that the prescriber is a certified prescriber, authorize, using the processor, the prescriber to prescribe to a patient the complement inhibitor. The computer device also comprises an interface configured to send an on-line transmission to the prescriber the prescription approval code.

In yet other aspects, a non-transitory computer-readable storage medium is provided, the medium storing instructions that, when executed by a processor of a computer device, cause the processor to (A) receive verification that a prescriber requesting to administer a complement inhibitor, such as eculizumab or an eculizumab variant, has agreed to the following conditions: (a) to vaccinate and/or revaccinate patients receiving the complement inhibitor, at predetermined times or intervals, with one or more meningococcal vaccines, including a meningococcal vaccine to *Neisseria meningitidis* serogroup B; (b) to provide patients with educational materials regarding eculizumab or an eculizumab variant, and (c) that the prescriber has reviewed information relating to administering the complement inhibitor; (B) access a database of certified prescribers; and add the prescriber to the database; (C) inspect the database of certified prescribers in response to a requisition from the prescriber requesting that the prescriber be provided with eculizumab or an eculizumab variant; and (D) authorizing the prescriber to prescribe eculizumab or an eculizumab variant only if the prescriber is in the database of certified prescribers.

In yet other aspects, a method is provided, comprising receiving a request from a patient enrolled in treatment plan of a complement inhibitor, such as eculizumab or an eculizumab variant, to be enrolled in a safety support program; adding, using a computer device with a processor suitably programmed to perform the adding, the patient to a patient safety registry; and prompting, using the processor, an authorized user to follow up with the patient to discuss the possibility of adverse events associated with the complement inhibitor, the prompting instructing the authorized user to discuss symptoms of the adverse events, and whether the patient has experienced an unreported adverse event, the prompting performed at one or more predetermined times or intervals.

A *Neisseria* meningococcal type B specific vaccine can be any meningococcal vaccine to *Neisseria meningitidis* serogroup B. In certain embodiments, the *Neisseria* meningococcal type B specific vaccine is multicomponent meningococcal serogroup B vaccine (4CMenB or BEXSERO®) or meningococcal group B vaccine (*Neisseria meningitidis* serogroup B recombinant lp2086 a05 protein variant antigen and *Neisseria meningitidis* serogroup B recombinant lp2086 b01 protein variant antigen, or Trumenba®) (see U.S. Pat. No. 8,563,006).

In certain embodiments, the recommended indication and usage, dosage and administration, dosage forms and strength, and use in specific patient population of either BEXSERO® or Trumenba® should be followed. However, a healthcare professional may adjust the recommended indication and usage, dosage and administration, dosage forms and strength, and use in specific patient population of either BEXSERO® or Trumenba® as needed.

According to certain embodiments, a complement-inhibitor-based treatment plan is coupled with a risk evaluation and management strategy ("REMS") and a safety support program ("SSP") for reinforcing the REMS. Using exemplary embodiments described herein, a risk of adverse events (especially, but not limited to, meningococcal infections) can be managed and an incidence of the adverse events can be reduced.

In exemplary embodiments, aspects of the REMS may be monitored and enforced using a software tool. An exemplary REMS software tool can monitor for, and/or enforce, one or more of the following requirements:

Mandatory vaccination against meningococcal infection, including for *Neisseria meningitidis* serotype B, Performance-linked drug distribution to ensure vaccination of patients, Direct heightened surveillance with monitoring for early signs of meningococcal infection, including by *Neisseria meningitidis* serotype B, coupled with immediate evaluation of suspected infection followed by antibiotic treatment, if necessary, Educational materials for both healthcare professionals and patients regarding infection risks, and/or Evaluation and monitoring of patients who discontinue complement-inhibitor-based treatment.

Aspects of the SSP may also be monitored and enforced using a software tool. The SSP software tool may connect to a database of registered nurses responsible for performing actions under the SSP. An exemplary SSP software tool may prompt one of the registered nurses in the database to perform one or more of the following actions:

Make calls to patients at predetermined times (e.g., monthly) or as allowed by the patient to ensure that the patient has a copy of related patient safety information, to review signs and symptoms of meningococcal infection, including by *Neisseria meningitidis* serotype B, and to encourage the patient to voluntarily report adverse events to the nurse care manager, and/or Monitor patient vaccination dates and send a revaccination reminder letter to the patient's health care provider by 3 years after the previous vaccination date.

In combination, the REMS and the SSP are effective in encouraging safe practices, such as pre-treatment vaccinations, that can mitigate the occurrence of adverse events during and after complement-inhibitor-based treatment. Another important effect of the REMS and SSP is an improvement in patient understanding of the risks and symptoms of adverse events. Some adverse events arising from the use of a complement inhibitor require early treatment. However, due to the nature of complement-inhibitor-based treatment, it may be especially difficult to achieve early treatment unless the patient is aware of these symptoms and has the tools to effectively seek early treatment. The REMS and SSP provide the patient with these tools.

In practice, the incidence of certain kinds of adverse events, such as meningococcal infections, has been reduced through implementation of the REMS and SSP.

Each of the above-described components (the complement-inhibitor-based treatment plan, the REMS software tool, and the SSP software tool) are described in more detail below.

Terminology

The present invention is directed to methods for the delivery of drugs, especially drugs inhibiting complement activation pathways, to patients. The term "drug," as used herein, refers to any substance which is intended for use in the diagnosis, cure, mitigation, treatment or prevention of disease, or to affect the structure or function of the body. Generally speaking, these methods are desirably and advantageously used to educate and reinforce the actions and behaviors of patients who are taking the drug, as well as prescribers who prescribe the drug and pharmacies which dispense the drug. Such education and reinforcement of actions and behavior are often necessary to ensure proper prescribing and dispensing of the drug, as well as patient compliance with taking the drug. In certain cases it is also necessary to educate patients and prescribers concerning discontinuation of the drug. Discontinuation of a drug may lead to harmful effects and the patient and prescriber need to be educated as to what these harmful effects may be, how to monitor for harmful effects, and how to treat the patient if harmful effects are seen upon discontinuation. A wide variety of educational materials may be employed to ensure proper prescribing, dispensing, patient compliance and follow-up observation, including, for example, a variety of literature and other materials, such as, for example, product information, package inserts, educational brochures, continuing education monographs, videotapes and the like which may describe the risks and benefits associated with taking and/or discontinuing the particular drug.

These methods and systems are employed for the distribution of a complement inhibitor to a patient. The term "complement inhibitor" refers to any agent (e.g., any nucleic acids, amino acids, polynucleotides, polypeptides, proteins, chemical compounds, etc.) which is capable of at least partially reducing, neutralizing, antagonizing or completely inhibiting the activation of complement activation pathways, e.g., the classical pathway, the alternative pathway, and the lectin pathway. Thus, the complement inhibitor can be any inhibitor that antagonizes any component in the complement activation pathways, resulting in a decreased level of downstream complement activation products. For example, a complement inhibitor may generally and broadly inhibit the complement activation at the level of C1 esterase, C3, or selectively block C5 activation with subsequent inhibition of C5a and C5b-9 (TCC) formation. One example of such inhibitors is an antibody or antigen-binding fragment thereof or antigen-binding polypeptide which binds to the cleavage site of C5 and thereby inhibits cleavage of C5 by preventing the C5 convertase from accessing the cleavage site in C5. Such inhibitors also include an antibody or antigen-binding fragment thereof or antigen-binding polypeptide, which binds to C5 and inhibits the activity of C5a and/or C5b fragment. Another example is an antibody or antigen-binding fragment thereof which binds to C5 at a site other than the cleavage site but prevents cleavage of C5. The antibodies eculizumab and pexelizumab, and variants thereof, are examples of such antibodies. Other complement inhibitors may antagonize or inhibit activators of complement pathways. One non-limiting example of such inhibitors is an antibody, antigen-binding fragment, antigen-binding polypeptide, or agent which recognizes and inhibits factor B or factor D. Some naturally occurring regulators include, for example, C1 inhibitors, complement receptor 1 (CR1/CD35), complement receptor 2 (CR2/CD21), membrane cofactor protein (MCP/CD46), decay-accelerating factor (DAF/CD55), factor I, factor H, C4BP, complement receptor 1 related gene/protein (Crry), CD59, microbial proteins, etc. Recombinant regulators may also be designed based on the natural regulators. For example, soluble proteins (e.g., soluble CR1, DAF, CD59, etc.), tagged proteins (e.g., with a glycosylphosphatidylinositol (GPI) anchor for specific targeting to cell surface), or fusion proteins comprising at least one regulator can be constructed and prepared using well-known methods in the art. Dominant negative proteins (e.g., containing a dominant negative mutation or truncation) of natural regulators can also be used as inhibitors of the corresponding endogenous proteins. Furthermore, chimeric proteins containing at least one inhibitor and at least one other agent (e.g., an agent as a targeting moiety for a specific cell/tissue type or to increase the stability or efficacy of the chimeric protein) could be constructed. In some embodiments, the recombinant complement inhibitor is an antibody or antigen-binding fragment thereof specifically recognizing at least one complement pathway component, such as, for example, mannose-binding lectin (MBL), C1, C3, C3 convertase, C5, C5 convertase, C5a, C5b-9 (TCC), factor D, factor B, etc. Such specific recognizing and binding by complement inhibitors may lead to an inhibition of the activation of certain complement pathway components or the formation of various species, such as certain protein complexes. The complement inhibitor of this application also includes small molecule inhibitors, for example, C1 binding peptides, compstatin, C3aR antagonists, C5aR antagonists, other small molecule inhibitors of complement components, etc. For a detailed discussion of possible complement inhibitors, see Mollnes and Kirschfink, 2006, Strategies of therapeutic complement inhibition, *Molecular Immunology* 43: 107-121.

In certain embodiments, the complement inhibitor is an antibody (or antigen-binding fragment thereof) that specifically binds to C5 (such as human C5). In one embodiment, the antibody or antigen-binding fragment thereof is the mouse anti-C5 monoclonal antibody BB5.1 (Frei et al., 1987, *Mol. Cell. Probes* 1: 141-149), the humanized anti-C5 single chain fragment h5G1.1-scFv (i.e., pexelizumab, Alexion Pharmaceuticals, Cheshire, Conn.), or the humanized anti-C5 monoclonal antibody eculizumab (with the commercial name Soliris®, Alexion Pharmaceuticals, Inc.), or an antigen-binding fragment thereof. Other C5 binding molecules and anti-C5 antibodies include, for example, C5 binding molecules and anti-C5 antibodies described in U.S. Patent Application Publication Nos. 20100034809 and 20100166748, in U.S. Pat. No. 7,999,081, and in Würzner et al. 1991, *Complement Inflamm.* 8:328-340.

In certain embodiments, the complement inhibitor is a polypeptide comprising an amino acid sequence with at least about 50% (e.g., 50, 55, 60, 65, 70, 75, 80, 85, 90, 95, or above 95%) homology (similarity) or identity with eculizumab or an eculizumab variant or pexelizumab. In other embodiments, the complement inhibitor comprises an amino acid sequence with at least about 75% homology or identity with eculizumab or an eculizumab variant or pexelizumab. The complement inhibitor may comprise in other instances an amino acid sequence with at least about 80% homology or identity therewith and in other embodiments at least about 85%, 90% or 95% homology or identity therewith. While the term "complement activation" or similar terms used herein in general refers to the activation of at least one of the complement pathways and at least one of the downstream complement components, the term "inhibiting complement activation by antagonizing C5" or similar terms used herein specifically refers to inhibiting the cleavage of C5 into C5a and C5b by C5 convertase and inhibiting downstream C5b-9 complex formation or inhibiting the formation of C5a or the activity of C5a.

In certain embodiments, the complement inhibitor is an antigen-binding fragment of eculizumab or an antigen-binding variant of eculizumab (also referred to herein as an eculizumab variant or a variant eculizumab, or the like).

In certain embodiments, the complement inhibitor is a variant derived from eculizumab, having one or more improved properties (e.g., improved pharmacokinetic properties) relative to eculizumab. The variant eculizumab antibody (also referred to herein as an eculizumab variant, a variant eculizumab, or the like) or C5-binding fragment thereof is one that: (a) binds to complement component C5; (b) inhibits the generation of C5a; and can further inhibit the cleavage of C5 into fragments C5a and C5b. The variant eculizumab antibody can have a serum half-life in a human that is greater than, or at least, 10 (e.g., greater than, or at least, 11, 12, 13, 14, 15, 16, 17, 18, 19, 20, 21, 22, 23, 24, 25, 26, 27, 28, 29, 30, 31, 32, 33 or 34) days. Such variant eculizumab antibodies are described in U.S. Pat. No. 9,079,949.

In yet other embodiments, the C5 inhibitor is LFG316 (Novartis, Basel, Switzerland, and MorphoSys, Planegg, Germany) or another antibody defined by the sequences of Table 1 in U.S. Pat. Nos. 8,241,628 and 8,883,158, ARC1905 (Ophthotech, Princeton, N.J. and New York, N.Y.), which is an anti-C5 pegylated RNA aptamer (see, e.g., Keefe et al., *Nature Reviews Drug Discovery* 9, 537-550 (July 2010) doi:10.1038/nrd3141), Mubodina® (Adienne Pharma & Biotech, Bergamo, Italy) (see, e.g., U.S. Pat. No. 7,999,081), rEV576 (coversin) (Volution Immuno-pharmaceuticals, Geneva, Switzerland) (see, e.g., Penabad et al., *Lupus,* 2014 October; 23(12):1324-6. doi: 10.1177/ 0961203314546022.), ARC1005 (Novo Nordisk, Bagsvaerd, Denmark), SOMAmers (SomaLogic, Boulder, Col.), SOB1002 (Swedish Orphan Biovitrum, Stockholm, Sweden), RA101348 (Ra Pharmaceuticals, Cambridge, Mass.), Aurin Tricarboxylic Acid ("ATA"), and anti-C5-siRNA (Alnylam Pharmaceuticals, Cambridge, Mass.), and Ornithodoros moubata C inhibitor ("OmCI").

The complement inhibitor is designed for treating or preventing a complement-associated disorder. This invention involves administering to a subject (e.g., a human) in need thereof a therapeutic complement inhibitor (e.g., an antibody or antigen-binding fragment thereof) in an amount sufficient to treat a complement-associated disorder afflicting the subject.

The complement-associated disorder can be, e.g., a complement-associated inflammatory disorder, paroxysmal nocturnal hemoglobinuria (PNH), atypical hemolytic uremic syndrome (aHUS), age-related macular degeneration (AMD), rheumatoid arthritis (RA), myasthenia gravis (MG), neuromyelitis optica (NMO), catastrophic anti-phospholipid syndrome (CAPS), anti-phospholipid syndrome (APS), viral hemorrhagic fever (such as Ebola hemorrhagic fever), or sepsis. In some embodiments, the complement-associated disorder is a complement-associated pulmonary disorder. For example, the complement-associated pulmonary disorder can be, e.g., asthma or chronic obstructive pulmonary disease (COPD). Other complement-associated disorders are also amenable to treatment or prevention.

The mode of administration can be any suitable mode, and can vary depending on the type of complement-associated disorder to be treated and the drug to be used. The mode of administration, can be, e.g., intravenous administration, intrapulmonary administration, intraocular administration, subcutaneous administration, or intraarticular administration.

In some embodiments, the complement inhibitor can be administered to a patient in conjunction with other therapies for complement-associated disorders. For example, the composition can be administered to a subject at the same time, prior to, or after, plasmapheresis, IVIG therapy, or plasma exchange. See, e.g., Appel et al. (2005) *J Am Soc Nephrol* 16:1392-1404. In some embodiments, the complement inhibitor can be administered to a subject at the same time, prior to, or after, a kidney transplant. The other, additional therapies can be any suitable therapy.

A "subject," as used herein, is a human, and is used interchangeably with the term "a patient." In some embodiments, the subject is an infant, adolescent, or adult.

The meningococcal vaccine to *Neisseria meningitidis* serogroup B can be any meningococcal vaccine to *Neisseria meningitidis* serogroup B. In certain embodiments, the meningococcal vaccine to *Neisseria meningitidis* serogroup B is BEXSERO® or Trumenba® (see U.S. Pat. No. 8,563, 006).

In certain embodiments, the recommended indication and usage, dosage and administration, dosage forms and strength, and use in specific patient population of either BEXSERO® or Trumenba® should be followed. However, a healthcare professional may adjust the recommended indication and usage, dosage and administration, dosage forms and strength, and use in specific patient population of either BEXSERO® or Trumenba® as needed.

In certain embodiments, "vaccination," "administering a vaccine," or the like, as used herein, refers to having fully complied with the dosage and frequency of administration as recommended by the manufacturer of the vaccine.

As used herein, a subject "in need of prevention," "in need of treatment," or "in need thereof," refers to one, who by the judgment of an appropriate medical practitioner (e.g., a doctor, a nurse, or a nurse practitioner in the case of humans; a veterinarian in the case of non-human mammals), would reasonably benefit from a given treatment (such as treatment with a composition comprising an anti-C5 antibody or antigen-binding fragment thereof).

The term "preventing" is art-recognized, and when used in relation to a condition, is well understood in the art, and includes administration of a composition which reduces the frequency of, or delays the onset of, symptoms of a medical condition in a subject relative to a subject which does not receive the composition. Thus, prevention of a complement-associated disorder such as asthma includes, for example, reducing the extent or frequency of coughing, wheezing, or chest pain in a population of patients receiving a prophylactic treatment relative to an untreated control population, and/or delaying the occurrence of coughing or wheezing in a treated population versus an untreated control population, e.g., by a statistically and/or clinically significant amount.

The terms "therapeutically effective amount," "effective amount," or "therapeutically effective dose," or similar terms used herein are intended to mean an amount of an agent (e.g., a complement inhibitor) that will elicit the desired biological or medical response (e.g., an improvement in one or more symptoms of a complement-associated disorder).

The term "patient certification" is intended to mean that (a) the patient, or the legal guardian or representative of the patient, is competent to comprehend and assess information and to make decisions; (b) the patient, or the legal guardian or representative of the patient, has received one or both of verbal and written warning as to the risk of adverse clinical events associated with discontinuing use of the complement inhibitor to treat the disorder; and (c) the patient, or the legal guardian or representative of the patient, has acknowledged the warning and agreement to the treatment.

The term "antibody" is well known in the art. For example, it refers to a whole or intact antibody (e.g., IgM, IgG, IgA, IgD, or IgE) molecule that is generated by any one of a variety of methods known in the art. The term "antibody" includes a polyclonal antibody, a monoclonal antibody, a chimerized or chimeric antibody, a humanized antibody, a deimmunized human antibody, and a fully human antibody. The antibody can be made in or derived from any of a variety of species, e.g., mammals such as humans, non-human primates (e.g., monkeys, baboons, or chimpanzees), horses, cattle, pigs, sheep, goats, dogs, cats, rabbits, guinea pigs, gerbils, hamsters, rats, and mice. The antibody can be a purified or a recombinant antibody, from any host cell, such as NSO cells and CHO cells.

As used herein, the term "antibody fragment," "antigen-binding fragment," or similar terms refer to a fragment of an antibody that retains the ability to bind to an antigen, e.g., a single chain antibody (scFv), an Fd fragment, an Fab fragment, an Fab' fragment, or an F(ab')$_2$ fragment. An scFv is a single polypeptide chain that includes both the heavy and light chain variable regions of the antibody from which the scFv is derived. In addition, diabodies (Poljak (1994) *Structure* 2(12):1121-1123; Hudson et al. (1999) *J Immunol Methods* 23(1-2):177-189), minibodies, triabodies (Schoonooghe et al. (2009) *BMC Biotechnol* 9:70), domain antibodies (also known as "heavy chain immunoglobulins" or camelids; Holt et al. (2003) *Trends Biotechnol* 21(11):484-490); and intrabodies (Huston et al. (2001) *Hum Antibodies* 10(3-4):127-142; Wheeler et al. (2003) *Mol Ther* 8(3):355-366; Stocks (2004) *Drug Discov Today* 9(22): 960-966) are included in the definition of antibody fragments and can be incorporated into the systems and used in the methods of this invention.

The antibodies and antigen-binding fragments thereof can be or can be made "chimeric." Chimeric antibodies and antigen-binding fragments thereof comprise portions from two or more different species (e.g., mouse and human). Chimeric antibodies can be produced with mouse variable regions of desired specificity fused to human constant domains (for example, U.S. Pat. No. 4,816,567). In this manner, non-human antibodies can be modified to make them more suitable for human clinical application (e.g., methods for treating or preventing a complement-mediated disorder in a subject).

Monoclonal antibodies include "humanized" forms of the non-human (e.g., mouse) antibodies. Humanized or CDR-grafted mAbs are particularly useful as therapeutic agents for humans because they are not cleared from the circulation as rapidly as mouse antibodies and do not typically provoke an adverse immune reaction. Generally, a humanized antibody has one or more amino acid residues introduced into it from a non-human source. These non-human amino acid residues are often referred to as "import" residues, which are typically taken from an "import" variable domain. Methods of preparing humanized antibodies are generally well known in the art.

Complement-Inhibitor-Based Methods

As described above, antibodies and biologically-active fragments can be used to treat a variety of complement-associated disorders such as, but not limited to: rheumatoid arthritis (RA); lupus nephritis; ischemia-reperfusion injury; paroxysmal nocturnal hemoglobinuria (PNH), atypical hemolytic uremic syndrome (aHUS); typical or infectious hemolytic uremic syndrome (tHUS); myasthenia gravis (MG); neuromyelitis optica (NMO); antiphospholipid syndrome (APS); Degos disease; catastrophic APS (CAPS); dense deposit disease (DDD); scleroderma; multiple sclerosis (MS); macular degeneration (e.g., age-related macular degeneration (AMD)); hemolysis, elevated liver enzymes, and low platelets (HELLP) syndrome; sepsis; dermatomyositis; diabetic retinopathy; thrombotic thrombocytopenic purpura (TTP); spontaneous fetal loss; Pauci-immune vasculitis; epidermolysis bullosa; recurrent fetal loss; multiple sclerosis (MS); sepsis, viral hemorrhagic fever (such as Ebola hemorrhagic fever), and traumatic brain injury. See, e.g., Holers (2008) *Immunological Reviews* 223:300-316 and Holers and Thurman (2004) *Molecular Immunology* 41:147-152. Also see PCT Publication No. WO2010/054403. In some embodiments, the complement-mediated disorder is a complement-mediated vascular disorder such as, but not limited to, a cardiovascular disorder, myocarditis, a cerebrovascular disorder, a peripheral (e.g., musculoskeletal) vascular disorder, a renovascular disorder, a mesenteric/enteric vascular disorder, revascularization to transplants and/or replants, vasculitis, Henoch-Schönlein purpura nephritis, systemic lupus erythematosus-associated vasculitis, vasculitis associated with rheumatoid arthritis, immune complex vasculitis, Takayasu's disease, capillary leak syndrome, dilated cardiomyopathy, diabetic angiopathy, thoracic-abdominal aortic aneurysm, Kawasaki's disease (arteritis), venous gas embolus (VGE), and restenosis following stent placement, rotational atherectomy, and percutaneous transluminal coronary angioplasty (PTCA). See, e.g., U.S. Pat. No. 7,919,094. In some embodiments, the complement-associated disorder is myasthenia gravis, cold-agglutinin disease (CAD), paroxysmal cold hemoglobinuria (PCH), dermatomyositis, scleroderma, warm autoimmune hemolytic anemia, Graves' disease, Hashimoto's thyroiditis, type I diabetes, psoriasis, pemphigus, autoimmune hemolytic anemia (AIHA), idiopathic thrombocytopenic purpura (ITP), Goodpasture syndrome, myasthenia gravis (MG), neuromyelitis optica (NMO), antiphospholipid syndrome (APS), Degos disease, sepsis (including septic shock), viral hemorrhagic fever (such as Ebola hemorrhagic fever) and catastrophic APS (CAPS).

In some embodiments, the complement inhibitor, alone or in combination with a second anti-inflammatory agent, can be used to treat an inflammatory disorder such as, but not limited to, RA (above), inflammatory bowel disease, sepsis (above), which includes septic shock, acute lung injury, disseminated intravascular coagulation (DIC), or Crohn's disease. In some embodiments, the second anti-inflammatory agent can be one selected from the group consisting of nonsteroidal anti-inflammatory drugs (NSAIDs), corticosteroids, methotrexate, hydroxychloroquine, anti-TNF agents such as etanercept and infliximab, a B cell depleting agent such as rituximab, an interleukin-1 antagonist, or a T cell costimulatory blocking agent such as abatacept (marketed as Orencia® by Bristol-Myers Squibb, New York, N.Y.).

In some embodiments, the complement-associated disorder is a complement-associated neurological disorder such as, but not limited to, amyotrophic lateral sclerosis (ALS), brain injury, Alzheimer's disease, myasthenia gravis (MG), neuromyelitis optica (NMO), and chronic inflammatory demyelinating neuropathy.

Complement-associated disorders also include complement-associated pulmonary disorders such as, but not limited to, asthma, bronchitis, a chronic obstructive pulmonary disease (COPD), an interstitial lung disease, α-1 anti-trypsin deficiency, emphysema, bronchiectasis, bronchiolitis obliterans, diffuse interstitial lung disease, alveolitis, sarcoidosis, pulmonary fibrosis, and collagen vascular disorders.

In one aspect, the disclosure features treating a patient with the complement inhibitor described herein (e.g., an anti-C5 antibody or antigen-binding fragment thereof, such as eculizumab or an eculizumab variant), wherein the patient is: (i) afflicted with, suspected of having, or at risk for developing a complement-associated disorder (e.g., PNH or aHUS); and (ii) in need of treatment.

In certain embodiments, the anti-C5 antibody for use in methods described herein is eculizumab. Eculizumab (Soliris®, Alexion Pharmaceuticals, Inc.), a humanized monoclonal antibody specifically recognizing human complement protein C5 and preventing the cleavage of C5 and the formation of C5a and the C5b-9 terminal complex, has been demonstrated to be effective in treating PNH and aHUS patients.

In certain embodiments, the anti-C5 antibody for use in methods described herein is a variant derived from eculizumab, having one or more improved properties (e.g., improved pharmacokinetic properties) relative to eculizumab. The variant eculizumab antibody (also referred to herein as an eculizumab variant, a variant eculizumab, or the like) or C5-binding fragment thereof is one that: (a) binds to complement component C5; (b) inhibits the generation of C5a; and can further inhibit the cleavage of C5 into fragments C5a and C5b. The variant eculizumab antibody can have a serum half-life in a human that is greater than, or at least, 10 (e.g., greater than, or at least, 11, 12, 13, 14, 15, 16, 17, 18, 19, 20, 21, 22, 23, 24, 25, 26, 27, 28, 29, 30, 31, 32, 33 or 34) days. Such variant eculizumab antibodies are described in U.S. Provisional Application No. 61/949,932.

Adverse effects resulting from complement inhibition may be directly related to the function of complement, i.e., increased susceptibility to infection and autoimmune- and immune-complex diseases, arising from impaired opsonization, adaptive immune response, tolerance or elimination of immune-complexes. The risk of infectious complications is most probably highest when blocking C3. Blocking of C5b-9 formation, however, could lead to increased susceptibility to certain pathogens, such as *Neisseriae*. In addition, Gram-negative septic shock may result from complement inhibition, while treatment with antibiotics would compensate for short-term complement inhibition.

For Soliris®, meningococcal infections are the most important adverse reactions experienced by patients while on the drug. In PNH clinical studies, the use of Soliris® increases a patient's susceptibility to serious meningococcal infections (septicemia and/or meningitis). The risk groups or the most known risk factors include: 1) genetic deficiency or therapeutic inhibition of terminal complement (such as Soliris® therapy); 2) lack of commercially available vaccine against meningococcal serogroup B (now available); and 3) delay or absence of appropriate medical consultation at the appearance of first symptoms. The occurrence of meningococcal infection can be prevented in some cases by means of meningococcal vaccines. For example, patients without a history of meningococcal vaccination can be vaccinated at least 2 weeks prior to receiving the first dose of Soliris® or other complement inhibitor. If urgent Soliris® therapy is indicated in an unvaccinated patient, the meningococcal vaccine should be administered as soon as possible. In patients who cannot receive meningococcal vaccine, including children below the age of two years, antibiotic prophylaxis could prevent meningococcal infection. However, meningococcal vaccination reduces, but does not eliminate, the risk of meningococcal infections. In clinical studies, 2 out of 196 PNH patients developed serious meningococcal infections while receiving treatment with Soliris®, both of whom had been vaccinated. In clinical studies among non-PNH patients, meningococcal meningitis occurred in one unvaccinated patient. In addition, a previously vaccinated patient with aHUS developed meningococcal sepsis during the post-study follow-up period.

Since anti-C5 antibodies or antigen-binding fragments (e.g., eculizumab and pexelizumab) block terminal complement activation, patients treated with these agents (e.g., eculizumab/Soliris®) may have increased susceptibility to infections in addition to meningococcal infections, especially with encapsulated bacteria. For example, children or adolescent patients may be at increased risk of developing serious infections due to *Streptococcus pneumonia* and *Haemophilus influenza* type b (Hib). In clinical studies, a total of 11 out of 195 PNH patients experienced an infection-related serious adverse event (SAE) with eculizumab treatment, including Cellulitis (1 patient), *Haemophilus* infection (1 patient), other infection (1 patient), Meningococcal sepsis (2 patients), Necrotizing fasciitis (1 patient), respiratory tract infection (1 patient), urinary tract infection (1 patient), viral infection (2 patients), and viral upper respiratory tract infection (1 patient). One out of 37 aHUS patients treated with eculizumab was found to have peritonitis. Correspondingly, vaccinations for the prevention of these infections should be administered prior to the treatment by terminal complement C5 inhibition.

The Soliris® therapy has been found to increase the number of PNH cells. Actually, the proportion of PNH RBCs increased among Soliris®-treated PNH patients by a median of 28% from baseline (range from −25% to 69%). Thus, PNH patients who discontinue treatment with Soliris® may be at increased risk for serious hemolysis. Serious hemolysis is identified by serum lactic dehydrogenase (LDH) levels greater than the pre-treatment level, along with any of the following: greater than 25% absolute decrease in PNH clone size (in the absence of dilution due to transfusion) in one week or less; a hemoglobin level of <5 gm/dL or a decrease of >4 gm/dL in one week or less; angina; change in mental status; a 50% increase in serum creatinine level; or thrombosis. Therefore, any PNH patient who discontinues Soliris® should be monitored for at least 8 weeks to detect serious hemolysis and other reactions. If serious hemolysis occurs after Soliris® discontinuation, consider the following procedures/treatments: blood transfusion (packed RBCs), or exchange transfusion (if the PNH RBCs are >50% of the total RBCs) by flow cytometry; anticoagulation; corticosteroids; or reinstitution of Soliris®. In clinical studies, 16 of 196 PNH patients discontinued treatment with Soliris®. Patients were followed for evidence of worsening hemolysis and no serious hemolysis was observed.

Disclosed herein is an unexpected discovery that some types of adverse reactions, including some severe ones, occur after discontinuation of the treatment of aHUS patients by inhibiting terminal complement C5. For example, severe thrombotic microangiopathy (TMA) complications were observed after Soliris® discontinuation in aHUS clinical studies. The reported severe TMA complications after drug discontinuation included: 1) graft failure requiring dialysis; 2) renal insufficiency; 3) end stage renal disease; 4) respiratory distress requiring intubation; 5) diarrhea and increased renal insufficiency; and 6) nephrotic syndrome and renal insufficiency. Severe TMA complications post discontinuation were identified by (i) any two or more measurements of any one of the following: a decrease in platelet count of 25% or more as compared to either baseline or to peak platelet count during eculizumab treatment; an increase in serum creatinine of 25% or more as compared to baseline or to nadir during eculizumab treatment; or, an increase in serum LDH of 25% or more as compared to baseline or to nadir during eculizumab treatment; or (ii) any one of the following: a change in mental status or seizures; angina or dyspnea; or thrombosis. In aHUS clinical studies, 18 patients (5 in the prospective studies) discontinued Soliris® treatment. Seven (7) severe TMA complications were observed following the discontinuation of Soliris® in 5 patients at a median of 33 days (range 27-80 days) following the last dose. Soliris® treatment was re-initiated in 4 of these 5 patients. However, no fatalities were reported in the aHUS clinical trials as result of severe TMA complications.

Additionally, similar TMA complications post discontinuation have now been seen in patients enrolled in clinical trials evaluating the use of Soliris® to treat patients who have NMO or MG.

The term "baseline" for different laboratory parameters used in the present disclosure is the last value available for the patient prior to initiation of treatment.

Some clinical parameters may be helpful for laboratory monitoring of PNH and aHUS with or without Soliris® treatment. For example, for PNH, serum LDH levels increase during hemolysis and may assist in monitoring Soliris® effects, including the response to discontinuation of therapy. In clinical studies, six patients achieved a reduction in serum LDH levels only after a decrease in the Soliris® dosing interval from 14 to 12 days. All other patients achieved a reduction in serum LDH levels with the 14 day dosing interval. For aHUS, early signs of thrombotic microangiopathy (TMA) include a decrease in platelet count, and increases in serum LDH and creatinine levels. Thus, patients should be followed for signs of TMA by monitoring the above laboratory parameters during Soliris® therapy and/or therapy discontinuation.

If TMA complications occur after Soliris® discontinuation, the re-initiation of the drug, with the same or a different regimen (e.g., dosage, injection method and frequency, etc.) should be considered. In addition, other available therapies include, for example, plasma therapy (e.g., plasmapheresis, plasma exchange, fresh frozen plasma infusion, etc.) or appropriate organ-specific supportive measures.

For safety concerns, pharmacovigilance has to be maintained for aHUS patients. For example, aHUS patients will be registered into a database and information regarding their risk factors (e.g., laboratory parameters regarding aHUS symptoms, related diseases, adverse reactions during therapy or after therapy discontinuation, therapy regimens, adverse events or state of well-being) may be collected. The information in the database may be updated, if necessary, and provided, if necessary, to any drug manufacturer, supplier, prescriber, aHUS patient (or the patient's legal guardian, representative, or supervising practitioner) as well as regulatory authorities.

The methods disclosed herein involve, inter alia, registering in a computer readable storage medium prescribers who are qualified to prescribe the involved complement inhibitor drugs including, for example, eculizumab (Soliris®), pexelizumab, biosimilar equivalents of eculizumab or pexelizumab, an eculizumab variant, other C5-binding molecules and anti-C5 antibodies or antigen-binding fragments thereof, e.g., those disclosed in U.S. Patent Application Publication Nos. 20100034809 and 20100166748, in U.S. Pat. No. 7,999,081, and in Würzner et al. *Complement Inflamm.* 8:328-340 (1991). Once registered in the computer readable storage medium, the prescriber, now called a certified prescriber, is eligible to prescribe the drug to patients in need of the drug. Generally speaking, to become registered in the computer readable storage medium, the prescriber is required to comply with various aspects of the methods described herein including, for example, providing patient education and counseling, and the like, as described in detail below. The registration of the prescriber in the computer readable storage medium may be achieved by providing the prescriber, for example, by hand, mail, facsimile transmission, or on-line transmission, with a registration card or form, together with appropriate educational materials concerning, for example, the particular drug for which the prescriber is being registered to prescribe, as well as suitable methods for delivering the drug to the patient, including the drug delivery methods described herein. The prescriber completes the registration card or form by providing information requested therein, and the registration card or form is returned to the manufacturer or distributor of the drug, or other authorized recipient of the registration materials, for example, by hand, mail, facsimile transmission or on-line transmission. Information which may be requested of the prescriber in the registration card or form may include, for example, the prescriber's name, address, and affiliation, if any, with one or more health care institutions. The prescriber's information in the registration card or form is then entered into the computer readable storage medium. It is contemplated that the registration of the prescriber into the computer readable storage medium may also be achieved, for example, by telephone. Suitable computer readable storage media which may be employed for registration of the prescribers (as well as the pharmacies and patients, as discussed herein) will be apparent to one of ordinary skill in the art, once armed with the teachings of the present application.

In accordance with the methods described herein, pharmacies which may fill prescriptions for the particular drug being prescribed herein can also be registered in a computer readable storage medium. The computer readable storage medium in which the pharmacies are registered can be the same as, or different from, the computer readable storage medium in which the prescribers are registered. Once registered in the computer readable storage medium, the pharmacy is eligible to dispense the involved drug to patients who are in need of the drug. Generally speaking, to become registered in the computer readable storage medium, the pharmacy is required to comply with various aspects of the methods described herein including, for example, registering the patient (also can be done in a computer readable storage medium), as well as other aspects of the present methods, as described in detail below. As with the registration of the prescriber in the computer readable storage medium, the registration of the pharmacy is achieved by providing the pharmacy, for example, by hand, mail, facsimile transmission, or on-line transmission, with a registration card or form, together with appropriate educational materials concerning, for example, the particular drug for which the pharmacy is being registered to dispense, as well as suitable methods for delivering the drug to the patient, including the drug delivery methods described herein. The pharmacy then completes the registration card or form by providing the information requested therein, which thereafter is returned to the manufacturer or distributor of the drug, or other authorized recipient of the registration card or form, for example, by hand, mail, facsimile transmission or on-line transmission. Information which may be requested of the pharmacy in the registration card or form may include, for example, the pharmacy's name, address, and affiliation, if any, with any health care institution such as, for example, hospital, health care organization, and the like. The pharmacy's information in the registration card or form is then entered into the computer readable storage medium. It is contemplated that the registration of the pharmacy into the computer readable storage medium may also be achieved, for example, by telephone.

As noted above, the drug-distributing methods described herein also can involve the registration of the patient in a computer readable storage medium. The registration of the patient can be carried out by the registered pharmacy at the time of the patient's initial visit to the pharmacy or by the prescriber if the prescriber obtains the drug and administers it to the patient. The computer readable storage medium in which the patients are registered may be the same as, or different from, the computer readable storage medium in which the prescriber and/or pharmacy is registered. Once registered in the computer readable storage medium, the patient in need of a particular complement inhibitor drug including, for example, a particular anti-C5 antibody or antigen-binding fragment thereof, may be eligible to receive the drug. Generally speaking, to become registered in the computer readable storage medium, the patient is required to comply with various aspects of the methods described herein. In certain embodiments, the pharmacy or prescriber will typically have a registration form filled out for the patient, which includes information on the patient, such as the patient's name, mailing address, date of birth, and the like. Information on the prescriber or dispensing pharmacy, such as the information described above for the registration thereof, may also be desirably entered on the patient registration form. The completed form may then be forwarded to the manufacturer or distributor of the drug, or other authorized recipients of the registration form by, for example, hand, mail, facsimile transmission or on-line transmission. It is contemplated that the registration of the patient into the computer readable storage medium may also be achieved, for example, by telephone.

In accordance with the methods of the present disclosure, the delivery of the drug to the patient may involve the following steps. As a prelude to prescribing and dispensing the drug to the patient, the prescriber and/or the pharmacy are registered in one or more appropriate computer readable storage media. Suitable computer readable storage media described herein are apparent to one of ordinary skill in the art, once armed with the teachings of the present application. If the prescriber is not registered in the computer readable storage medium, the prescriber is ineligible to prescribe the drug. Similarly, if the pharmacy is not registered in the computer readable storage medium, the pharmacy is ineligible to dispense the drug.

In the course of an examination of a patient, including patients suffering from one or more diseases and/or disorders relevant to complement activation such as, for example, PNH or aHUS, the prescriber may determine that the patient's condition would be improved by the administration of a drug described herein, including eculizumab (Soliris®) or an eculizumab variant. Prior to prescribing the drug, the prescriber may counsel the patient, for example, on the various risks and benefits associated with the drug. For example, the prescriber preferably discusses the benefits associated with taking the drug, while also advising the patient of the various side effects associated therewith. Thus, a patient who may acquire or impart a condition or disease for which the drug is contraindicated is preferably counseled by the prescriber on the dangers associated therewith. For example, in the case of complement inhibitors antagonizing C5 (e.g., eculizumab (Soliris®), an eculizumab variant, pexelizumab, or other anti-C5 antibodies described herein), the prescriber may counsel the patient on the dangers of being administered the drug without vaccination against various bacterial-induced infections (e.g., Meningococcal infection, including an infection by *Neisseria meningitidis* serotype B) and the dangers of the potential severe hemolysis or severe TMA complications after treatment discontinuation. Such counsel may be provided verbally, as well as in written form. In certain embodiments, the prescriber provides the patient with literature materials on the drug for which a prescription is contemplated, such as product information, package insert, educational brochures, patient instruction videos, and the like. Thus, in the case of methods involving complement inhibitors, the prescriber preferably provides patients with literature information, for example, in the form of the aforesaid product information, package insert, educational brochures, patient instruction videos, and the like, warning the patient of the effects and/or the adverse effects during the treatment and/or after treatment discontinuation of the inhibitor.

With particular reference to counseling provided in connection with the complement inhibitor drug (e.g., eculizumab (Soliris®), an eculizumab variant, pexelizumab, biosimilar equivalents of eculizumab or pexelizumab, or other anti-C5 antibodies or antigen-binding fragments thereof described herein), the prescriber can counsel aHUS patients that have already discontinued inhibitor treatment or will discontinue the treatment in future. If the patient has already discontinued the inhibitor treatment or will soon discontinue the treatment (for example, it is reasonably believed that the patient will discontinue the treatment in 1, 2, 3, 4, 5, 6, 7, or more days, or 1, 2, 3, 4, 5, 6, or more weeks), the prescriber can counsel and/or remind the patient more frequently as the expected discontinuation date approaches or after the actual discontinuation date. Further, the patient can be counseled to have his or her risk factors for the adverse effects after discontinuation (e.g., the various laboratory parameters described herein) measured by himself/herself, a professional personnel, an organization, or a facility authorized by the drug supplier, the prescriber, or the distributor (e.g., a nurse, a doctor, a hospital, a medical laboratory, or a pharmacy). The patient can be counseled to examine his/her risk factors, including for multiple times or continuously for a reasonable time period, for identification of possible adverse reactions after discontinuation. The drug supplier, the prescriber, and/or the distributor preferably help to provide directions or such professional personnel or organization for measuring the risk factors of the patient, preferably periodically.

Once a patient is diagnosed to have, or reasonably predicted to have (e.g., based on various risk factors or laboratory parameters described herein), at least an adverse effect or reaction after treatment discontinuation, the diagnosis or the reasonable prediction (further including those measured risk factors or laboratory parameters, if any, in support of such diagnosis or prediction) is registered in a suitable computer readable storage medium, which can be in the same registry of the patient containing his or her previous clinical information. The patient is informed about the diagnostic result or the reasonable prediction (further including those measured risk factors or laboratory parameters, if any, in support of such diagnosis or prediction). Based on the registry of the diagnosis or the reasonable prediction, the patient is counseled for possible treatments or therapies for the adverse reaction. Such possible treatments or therapies include, for example, re-initiation of the same complement inhibitor treatment or therapy, substitute treatments or therapies with at least one different complement inhibitor or with a different regimen (e.g., a different dosage, injection method or frequency, etc.) of the same inhibitor, or substitute treatments or therapies involving different mechanisms or target molecules causing the disease or the adverse reaction. For example, for any adverse reaction experienced or to be experienced (based on reasonable predictions) by an aHUS patient discontinuing Soliris® treatment, the possible treatments or therapies include, for example, re-initiation of the same Soliris® treatment, a Soliris® treatment with a different regimen, substitute treatments with pexelizumab or a different anti-C5 antibody or antigen-binding fragment thereof or a different complement inhibitor, or substitute therapies including, for example, plasma therapy (e.g., plasmapheresis, plasma exchange, fresh frozen plasma infusion, etc.) or appropriate organ-specific supportive measures. If needed, a combination of the various treatments or therapies can be considered and administered to the patient.

As would be apparent to one of ordinary skill in the art, once armed with the teachings of the present application, one or more aspects of the counseling described above is applicable, in certain circumstances, for complement-inhibiting drugs other than Soliris®, an eculizumab variant, or other anti-C5 antibodies or antigen-binding fragments thereof.

"Counseling a patient" or "counsel a patient" or similar terms used herein is defined as counseling the patient or the patient's legal guardian(s)/representative(s). For all the counseling situations, the patient, or the patient's legal guardian(s)/representative(s), should be of age, as well as being in a physical and psychological state capable of apprehending the counseling correctly and precisely. The counseling includes receiving counseling on the drug being prescribed, and counseling, for example, on the adverse reactions after treatment discontinuation and prior to receiving a prescription for the drug. The methods disclosed herein require the patient, or the legal guardian(s) or representative(s) of the patient in case the patient is too young or physically or mentally incapacitated, to: 1) apprehend the information correctly and precisely; or 2) be legally responsible for his or her own behaviors, to express acknowledgment of the counseling and the warning of the adverse reactions while using the drug or discontinuing the usage of the drug. Both the counseling and the acknowledgement can be in verbal and/or written forms. The counseling may be through on-site consultation, telephone, mail, facsimile transmission, or on-line transmission. The counseling may, for example, when a patient is not directly supervised by a health professional and/or the prescriber, include literature materials on the drug for which a prescription is contemplated, such as product information, package insert, educational brochures, continuing education monographs, and the like. In certain embodiments, the content of the counseling is provided in the patient labeling of the drug and is distributed together with the drug. The patient, or the legal guardian(s) or representative(s) of the patient, is expected to express acknowledgement of counseling through on-site acknowledgement, telephone, mail, facsimile transmission, or on-line transmission, while at least one legally acceptable form of acknowledgement (for example, an original signature, an electronic signature, an oath or declaration before a notary, etc.) is submitted. For example, the patient or the patient's legal guardian(s) or representative(s) is expected to fill out an informed consent form which is signed by the prescriber, as well as the patient or the patient's legal guardian(s)/representative(s). The prescriber should retain a copy of the informed consent form for his/her records. By filling out and signing an informed consent form, the patient or the patient's legal guardian(s)/representative(s) acknowledges that he/she understands the risks associated with taking the drug or discontinuing the drug. In the informed consent form, the patient, or the patient's legal guardian(s) or representative(s) can agree to behave, or help the patient to behave, in a manner which is consistent with the prescriber's counsel. For example, in cases involving, for example, anti-C5 antibodies or antigen-binding fragments thereof (e.g., Soliris® and pexelizumab), the patient, or the patient's legal guardian(s) or representative(s), may express agreement to do, or agreement to help the patient to do, at least one of the following: i) monitor at least one risk factor or laboratory parameter for adverse reactions after discontinuing drug treatment; 2) report to the drug prescriber (including, if needed, the drug supplier and the drug distributor) the risk factor or laboratory parameter measurements and the time when the treatment discontinued or will be discontinued; and 3) consider and, if needed, agree to re-initiate the same treatment or a substitute treatment or therapy as described herein in case of experiencing or expecting to experience (based on reasonable predictions) at least one adverse reaction after treatment discontinuation.

In certain embodiments, the counseling described herein is delivered to the patient, or the patient's legal guardian(s) or representative(s), prior to both a new prescription and any future refill prescription. Any drug prescriber, distributor, packer, or authorized dispenser can be required to provide such counseling in one or both verbal and written formats (e.g., in the patient labeling) to the patient, or the legal guardian(s) or representative(s) of the patient, when a new prescription or refill prescription is dispensed. Any drug manufacturer or supplier can be further required to: 1) obtain approval from the drug regulatory agency (e.g., the U.S. FDA office or the corresponding governmental office in the country or region where the drug will be distributed) for the counseling which will be provided with the drug; and 2) ensure that the counseling information will be provided in sufficient numbers, or provide the means to produce the counseling information in sufficient numbers, to distributors, packers, and other authorized dispensers to permit these authorized dispensers to provide the counseling information to each prescriber and to each patient, or the legal guardian(s) or representative(s) of the patient, who will receive a drug prescription.

The counseling information or warning described herein, including, for example, the potential risk of adverse effects after discontinuing the complement inhibitor treatment, can be provided by any drug manufacturer, supplier, distributor, prescriber, authorized dispenser, or supervising practitioner (e.g., a licensed doctor or nurse or other practitioner) to any drug manufacturer, supplier, distributor, prescriber, authorized dispenser, supervising professional personnel, or patient who is taking or has a potential to take such drug.

A "provider" of a complement inhibitor, such as eculizumab or an eculizumab variant, can be a manufacturer, supplier, and/or distributor of that drug. For example, Alexion Pharmaceuticals is a provider for eculizumab and an eculizumab variant.

As used herein, the term "prescriber" refers to any individual who is capable of prescribing drugs, including, for example medical doctors. The term "authorized dispenser" used herein is intended to mean an individual, a facility, or an organization which is licensed, registered, or otherwise permitted by the jurisdiction in which the individual, facility, or organization practices to provide drug products on prescription in the course of professional practice. Authorized dispensers have the ability to authorized distribution of the complement inhibitor once the relevant regulatory agencies approve marketing of the complement inhibitor. The term "dispense to patients" or "prescription is dispensed," or similar terms used herein are intended to mean the act of delivering a prescription drug to a patient, or the patient's legal guardian(s) or representative(s), either: i) by a licensed practitioner or an agent of a licensed practitioner, either directly or indirectly, for self-administration by the patient, or the patient's legal guardian(s) or representative(s), or outside the licensed practitioner's direct supervision; or ii) by an authorized dispenser or an agent of an authorized dispenser under a lawful prescription of a licensed practitioner.

In certain embodiments, such counseling information or warning is provided in the drug label information of the complement inhibitor. Specifically, the prescription drug labeling information is also known as prescribing information, package insert, professional labeling, direction circular, package circular, etc. The term "label" or similar terms used herein are intended to mean a display of written, printed, or graphic matter upon the immediate container of any article or meant to include a package insert; and a requirement made by or under authority of U.S. Code of Federal Regulations and the U.S. Federal Food, Drug, and Cosmetic Act (FD&C Act) that any word, statement, or other information appearing on the label shall not be considered to be complied with unless such word, statement, or other information also appears on the outside container or wrapper, if any there be, of the retail package of such article, or is easily legible through the outside container or wrapper. The term "labeling" or similar terms used herein are intended to mean all labels and other written, printed, or graphic matters (1) upon any article or any of its containers or wrappers, or (2) accompanying such article, e.g., a package insert.

In certain other embodiments, such counseling information or warning, with or without patient information (e.g., bibliographic information, clinical record, personal and/or family disease and/or therapy record, the risk factors and/or laboratory parameters for disease diagnosing and/or monitoring, etc.) and/or the acknowledgement of the counseling or warning and agreement to the complement inhibitor treatment from the patient, are collected and stored, preferably in a database via a computer readable medium. In still certain other embodiments, such collected information is reported fully or partially to any drug manufacturer, supplier, distributor, prescriber, supervising professional personnel, patients who are taking or have a potential to take such drug, and/or any regulatory agencies (e.g., the U.S. FDA or the corresponding governmental offices in the country where the complement inhibitor is distributed). In certain other embodiments, such collected information is updated and/or modified (e.g. with updated patient information and/or any change in the acknowledgement and agreement from the patient, or with updated counseling information or warning based on postmarketing studies or research), preferably in a periodic manner, and reported as described herein.

The present disclosure also features a database prepared by the methods disclosed herein, via a computer readable medium, containing registered patients' information. Such patient information may include patient personal information (e.g., bibliographic information, personal or family disease and/or treatment record, and the fact or potential to have at least one of the adverse clinical events after discontinuing use of the complement-inhibiting drug) and the patient's acknowledgement of the potential adverse reactions after drug discontinuation and agreement to drug treatment as described herein. Such patient information can be updated, preferably periodically, and be provided to any relevant personnel, facility, organization, or authority as described herein.

In certain aspects, a method is provided to distribute a complement inhibitor to a physician or a pharmacy who can further distribute the inhibitor to a patient who needs the complement inhibitor, such as having a complement-associated disorder, to treat the patient. In some embodiments, the inhibitor can be authorized for distribution to the physician or pharmacy only upon certification from the physician or pharmacy that:
  i) the physician or pharmacy has received one or both verbal and written warning as to the risk of adverse clinical events associated with discontinuing use of the complement inhibitor to treat the disorder; and
  ii) the physician or pharmacy will distribute the warning to the patient, or the legal guardian or representative of the patient.

In certain embodiments, the certification and the information of the physician or pharmacy can be registered via a computer readable medium into a database. The physician or pharmacy can require a certification or acknowledgement of receiving and understanding of the warning disclosed herein and/or an agreement of the treatment from the patient, or the legal guardian or representative of the patient prior to or at the same time of distributing the complement-inhibiting drug to the patient, or the legal guardian or representative of the patient. Such certification or acknowledgement and/or agreement can be further submitted to the drug distributor, manufacturer, and/or regulatory authorities, who may register such information into a database via a computer readable medium. Preferably, such information, including the certification or acknowledgement and/or agreement from the physician (or pharmacy) or the patient (or the legal guardian or representative of the patient), or both, is to be received prior to or at the same time of or in a reasonable time frame after distributing the complement-inhibiting drug to the physician or pharmacy. In one embodiment, the certification is to be received after the distribution of the inhibitor to the physician or pharmacy but prior to the distribution of the inhibitor to the patient, or the legal guardian or representative of the patient.

The present disclosure also features a method of creating a database of physicians or pharmacies who can be allowed to distribute a complement inhibitor for use in treating a complement-associated disorder. In some embodiments, the database is registered via a computer readable medium containing information that the physicians or pharmacies have received and acknowledged one or both of verbal and written warning as to the risk of adverse clinical events associated with discontinuing use of a complement inhibitor to treat the disorder and agreed to distributing the warning to the patient who has the disorder, or the legal guardian or representative of the patient.

In a non-limiting example, the complement-associated disorder disclosed herein is a complement-associated inflammatory disorder, paroxysmal nocturnal hemoglobinuria (PNH), atypical hemolytic uremic syndrome (aHUS), age-related macular degeneration (AMD), rheumatoid arthritis (RA), myasthenia gravis (MG), neuromyelitis optica (NMO), catastrophic anti-phospholipid syndrome (CAPS), anti-phospholipid syndrome (APS), sepsis, a complement-associated pulmonary disorder, asthma, sepsis, viral hemorrhagic fever (such as Ebola hemorrhagic fever), or chronic obstructive pulmonary disease (COPD).

The present disclosure also features a database of physicians or pharmacies created by the methods disclosed herein.

The present disclosure also features a method to manufacture a complement inhibitor. The potential manufacturer should obtain an approval from a relevant government regulatory authority for manufacturing for sale the specific drug for the specific disease or indication. The regulatory authority (including, for example, the U.S. FDA and other corresponding agencies in the country or region where the drug will be manufactured and/or sold) will make a decision whether to approve this request based on the previously submitted drug information including, for example, the adverse clinical events after drug discontinuation and the patient information comprising the real events after drug discontinuation. Upon approval, the potential manufacturers may manufacture the complement-inhibiting drug in the approved country or region. Additionally, the manufacturer may be further required to produce or ensure the production of a document which provides a warning or caution comprising the whole or part of the information submitted to the regulatory authority, for example, the adverse clinical events after drug discontinuation. The manufacturer may be further required to provide the manufactured drug together with the produced document to any relevant personnel, facility, organization, or authority, if necessary.

The present disclosure also features a method to distribute the complement inhibitor described herein. The potential distributor should obtain an approval from a relevant government regulatory authority for distributing the specific drug for the specific disease or indication. The regulatory authority (including, for example, the U.S. FDA or other corresponding agencies in the country or region where the drug will be distributed) will make a decision whether to approve this request based on the previously submitted drug information including, for example, the adverse clinical events after drug discontinuation and the patient information comprising the real events after drug discontinuation. Upon approval, the potential distributor may distribute the complement-inhibiting drug in the approved country or region. Additionally, the distributor may be further required to produce or ensure the production of a document which provides a warning or caution comprising the whole or part of the information submitted to the regulatory authority, for example, the adverse clinical events after drug discontinuation. Alternatively, the distributor may receive the document from the relevant manufacturer or the authority. The distributor may be further required to provide the manufactured drug together with the produced document to any relevant personnel, facility, organization, or authority, if necessary.

As used herein, a "memory" refers to the physical devices used to store programs or data on a temporary or permanent basis for use in a computer or other digital electronic device. A "computer readable medium" refers to a medium capable of storing data in a format readable by a computer or a computer-related mechanical device. Examples of such computer readable media include magnetic media such as magnetic disks, cards, tapes, and drums, punched cards and paper tapes, optical disks (e.g., CD, CD-ROM, CD-R, CD-RW, DVD, etc.), and other media well known in the art. A person of ordinary skill in the art would readily appreciate that a computer readable medium includes a hard drive.

The present disclosure also features a system for distributing the disclosed complement inhibitor (CI1) for use in treating a patient afflicted with, suspected of having, or at risk for developing a complement-associated disorder, and in need of treatment with the complement inhibitor. As a non-limiting example, the system comprises a memory or a storage device for storing information about the patient and about whether an instruction to distribute the complement inhibitor is executed, and a processor configured to execute the instruction. In some embodiments, the instruction causes the processor to perform the steps comprising i) searching the memory or storage device for certifications that (a) the patient or the legal guardian or representative of the patient is competent to comprehend and assess information and to make decisions; (b) the patient, or the legal guardian or representative of the patient, has received one or both verbal and written warning as to the risk of adverse clinical events associated with discontinuing use of the complement inhibitor to treat the disorder; and (c) the patient, or the legal guardian or representative of the patient, has expressed acknowledgment of the warning and agreement to the treatment. The processor also ii) upon the identification of certifications in step i), authorizing distribution of the complement inhibitor to treat the patient; and iii) registering via the memory or storage device the distribution of the complement inhibitor.

The systems and methods disclosed herein can be implemented on a computer system, server, or other electronic device, that is capable of storing information or processing information. In some embodiments, the system includes one or more computer systems, servers, or other electronic devices capable of storing information or processing information.

The systems store information on paper or on a computer readable medium. The stored information may include, for example, the basic information and clinical record of the patient, the information about the manufacturer(s) who will manufacture the complement inhibitor, the information about the pharmacy(s) or the physician(s) who will distribute the complement inhibitor to the patient, the information about the distribution of the warning regarding the disclosed adverse clinical events to the patient, the legal guardian or representative of the patient, and/or the pharmacy(s) or the physician(s), and the acknowledgement of receiving of such information and/or agreeing to the treatment by the patient, its legal guardian or representative, and/or the pharmacy(s) or the physician(s). The system disclosed herein may further store information including, for example, the information about the discontinuing use of the complement inhibitor by the patient, the information that the patient is monitored for adverse clinical events prior to, at the same time of, or after the discontinuation, and the information that the patient is treated by re-initiation of the complement inhibitor (CI1) treatment or with an alternative therapy to treat the adverse clinical events after the discontinuing use of the complement inhibitor (CI1).

The information stored in the system disclosed herein can be collected in a voluntary or mandatory manner from the corresponding patient (or his or her legal guardian or representative), the manufacturer or distributor of the complement inhibitor, and/or the pharmacy or the physician who will distribute the complement inhibitor to the patient. The information can be stored and created, for example, into a database. The information can be reported to a government regulatory agency in a voluntary or mandatory manner. In some embodiments, a review of such reported information followed by an approval from the government regulatory agency is required prior to the distribution of the complement inhibitor. The collection and/or the submission of the information disclosed herein can be executed by hand, mail, telephone, facsimile transmission, or on-line transmission.

These and other embodiments of the invention are described below with reference to FIGS. 1-11 wherein like numerals are used throughout to denote like elements.

Figure 1B:
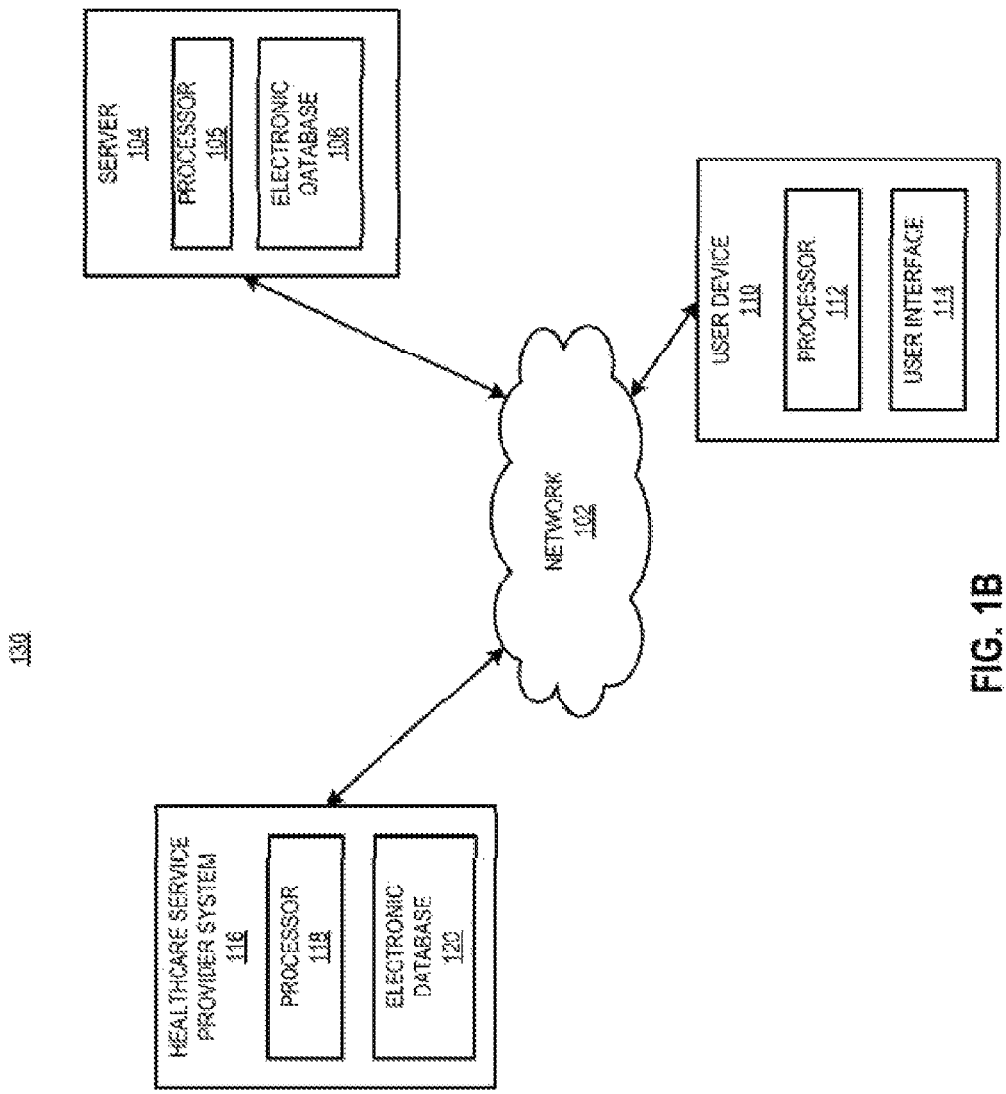

FIGS. 1A and 1B depict example network and database structures that may be used to implement the systems and methods disclosed herein and comprise systems 100 and 130. In particular, FIG. 1A is a block diagram of a computerized system 100 for authorizing the distribution of a drug to patients, according to an illustrative implementation. The system 100 includes a server 104 and for example and in a non-limiting way a selected number, such as three, user devices 110A-110C (generally, user device 110) connected over a network 102 to the server 104. The server 104 includes a processor 105 and an electronic database 106, and each user device 110 includes a processor 112 and a user interface 114, such as user interfaces 114A, 114B and 114C. As used herein, the term "processor" or "computing device" refers to one or more electronic devices, computing devices, computers, microprocessors, logic devices, servers, smart phones, tablets, or other devices configured with hardware, firmware, and/or software to carry out one or more of the computerized techniques described herein. Processors and processing devices may also include one or more memory devices for storing inputs, outputs, and data that is currently being processed. An illustrative computing device 1100, which may be used to implement any of the processors and servers described herein, is described in detail below with reference to FIG. 11. As used herein, "user interface" includes, without limitation, any suitable combination of one or more input devices (e.g., keypads, displays, touch screens, trackballs, voice recognition systems, and the like) and/or one or more output devices (e.g., visual displays, speakers, tactile displays, printing devices, and the like). As used herein, "user device" includes, without limitation, any suitable combination of one or more devices configured with hardware, firmware, and software to carry out one or more of the computerized techniques described herein. Examples of user devices include, without limitation, personal computers, laptops, and mobile devices (such as smartphones, blackberries, PDAs, tablet computers, and the like). One server and three user devices are shown in FIG. 1A. However, the arrangement and number of components shown in FIG. 1A are merely illustrative, and the system 100 can support multiple servers and any number of user devices in any suitable configuration.

The components of the system 100 of FIG. 1A may be arranged, distributed, and combined in any of a number of ways. For example, the components of system 100 may be distributed over multiple processing and storage devices connected via the network 102. Such an implementation may be appropriate for distributed computing over multiple communication systems including wireless and wired communication systems that share access to a common network resource. In some implementations, system 100 is implemented in a cloud computing environment in which one or more of the components are provided by different processing and storage services connected via the Internet or other communications system. For example, the server 104 may be implemented as virtual servers instantiated in a cloud computing environment. The electronic database 106 may be a distributed system of databases that includes data regarding patient information such as a patient's demographic features (such as date of birth, gender, height, weight, or any other demographic feature), diagnosis, prognosis, administered medications, symptoms, physicians, pharmacists, geographical location, or any other suitable data related to a patient. The improved availability associated with using distributed architecture advantageously facilitates continuous tracking and logging of inputs from various patients, physicians, pharmacists, or any other suitable representative of a patient.

The components of FIG. 1A may be implemented as one or more components included with or local to a user device 110. For example, FIG. 1A depicts a user device 110 that includes a processor 112 and a user interface 114. The processor 112 may be configured to perform any of the functions described herein for the user interface 114. Additionally, the functions performed by each of the components in system 100 may be rearranged. In some implementations, the processor 112 may perform some or all of the functions of the processor 105 as described herein. Any suitable variation of this system may be used.

A user provides user input over the user interface 114. The user may be the patient or a representative of the patient such as a legal guardian, physician, pharmacist, or nurse. The user input may include any data related to a patient. In particular, the user input includes data indicative of the patient's identity, such as the patient's name or an identification number associated with the patient such as a social security number, a healthcare insurance number, and the like. The processor 112 transmits this data over the network 102 to the server 104, and the processor 105 parses the electronic database 106 for a previous registration of the patient.

If the patient has been previously registered, the user provides data indicative of an event in the patient's care. For example, an event may include an administration of a drug, a symptom expressed by the patient, a measurement of a level of physiological parameter related to the patient, or any other suitable event (e.g., an adverse clinical event) related to the care of the patient. The event data is then transmitted over the network 102, received by the processor 105, and stored in the electronic database 106.

Alternatively, if the patient has not been previously registered, the user device 110 is configured to prompt the user to register the patient. Registration of a patient may require several electronic certifications over the user interface 114, including a certification that a representative of the patient is competent and can make decisions regarding the patient's treatment. In addition, the representative receives a warning regarding the risk of adverse clinical events associated with the use of a drug to treat the patient. Another possible required certification for registration of the patient is that the representative has acknowledged receipt of the warning. A third possible certification requires that the representative agrees to use the drug in treatment for the patient.

When registration is complete at the user interface 114, the processor 112 transmits the new patient's data over the network 102 to the server 104, where the data is stored in the electronic database 106 as a registered patient. Then, the processor 105 updates an electronic authorization variable associated with the registered patient, thereby authorizing distribution of the drug for use in treating the patient. The same user device 110 may be used to register different patients. Similarly, data regarding a given patient may be provided over multiple user devices 110 over the course of the patient's treatment. In this way, system 100 provides a secure method of authorizing distribution of a drug to patients with representatives who acknowledge a risk of adverse clinical events associated with the drug.

The components of system 130 illustrated in FIG. 1B are similar to those of FIG. 1A, with the exception that FIG. 1B additionally includes a healthcare service provider system 116 including a processor 118 and an electronic database 120. In some implementations, the healthcare service provider system 116 is configured to share patient-related data stored on the electronic database 120 with the server 104. In particular, the healthcare service provider system 116 may have additional data regarding a registered patient that have not been directly provided by a user device 110. For example, the user device 110 may have been used to register a patient for a particular disorder. At a later time, the same patient may be treated at a hospital for a different disorder, and the hospital may monitor patient treatments and symptoms. The hospital staff may have provided data indicative of the patient's treatment and/or symptoms to the healthcare service provider system 116, which stores the data on the electronic database 120. The data on the electronic database 120 is then shared with the server 104. By aggregating patient-related data across different sources, the server 104 is more likely to maintain an updated patient history and achieves a more accurate patient profile.

The patient data stored on the electronic databases 106 and 120 may include private and classified information, and it is desirable to maintain a degree of confidentiality. The systems 100 and 130, and every system disclosed herein, are configured to comply with any privacy or confidentiality laws that may exist in the jurisdiction in which the system is installed. In some implementations, all data in relation to all patients is processed using encryption and decryption algorithms to ensure secure data transmission over the network 102.

FIG. 2 depicts a data structure 200 for records in a patient database, which may be stored in the electronic database 106. The data structure 200 includes a list of patient identification numbers, representative identification numbers, and patient-related data, such as age, gender and the like. Upon registration, each patient may be labeled with a patient identification number, and in addition, the representative of each patient may also be labeled with a representative identification number. For example, the representatives of the patients 1254 and 574 may be legal guardians, physicians, pharmacists, or any other suitable representative. In addition, a patient may be his/her own representative, as is the case with patient 1345.

The data structure 200 further includes the ages and genders of the patients, and a flag variable representative of whether the patient is registered. For registered patients, a date indicating the beginning of the administration of the drug and a date indicating the discontinuation of the drug administration are also recorded, if applicable. For example, the patients 1254 and 1345 were administered the drug for an amount of time before discontinuation, and the treatment of patient 576 still includes the use of the drug. The patient 687 has not yet been registered, and so there is no corresponding representative identification number or dates of beginning and discontinuation of drug administration.

The data structure 200 may also include further patient-related information, such as dates of actual administration of the drug, doses of the administered drug, patient symptoms, or any other suitable patient-related information. In particular, the data structure 200 may be updated periodically with data generated from patient reports that may be prepared by the patient or a representative of the patient, or by the health service provider. In this way, the data structure 200 may track the progression of a patient throughout the patient's treatment. By storing patient-related data in this way, the system 100 provides a method for monitoring a patient's progress during treatment and also provides a rich database with information that may provide insight for future decisions regarding the same patient or a patient with similar characteristics.

Figure 3:
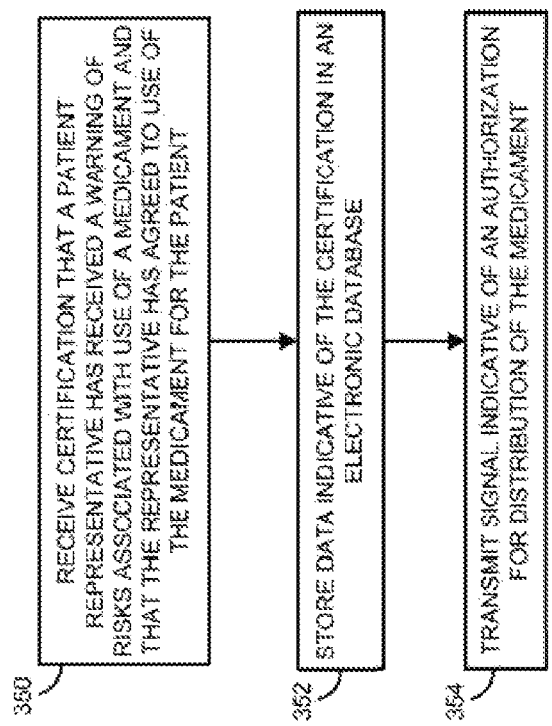
FIG. 3 is a flowchart of an exemplary method to authorize distribution of a drug for use in treating a patient.

FIG. 3 is a flowchart of a method 300 that may be implemented by the server 104 to authorize distribution of a drug for use in treating a patient. The method 300 includes the steps of receiving certification that a patient representative has received a warning of risks associated with use of a complement inhibitor (or a drug) and that the representative has agreed to use of the complement inhibitor for the patient (step 350), storing data indicative of the certification in an electronic database (step 352), and transmitting a signal indicative of an authorization for distribution of the complement inhibitor (step 354).

At step 350, the server 104 receives certification from a user device 110 that a representative of a patient has received a warning regarding the risks associated with the use of a complement inhibitor. Furthermore, the server 104 also receives certification that the representative has agreed to the use of the complement inhibitor in treatment for the patient. In particular, the representative may be required to provide an acknowledgment of receipt of the warning as well as agreement to use of the complement inhibitor in the form of a signature or any other suitable form of certification. Various types of certifications that can be used in the systems of the present invention would be readily apparent to one of ordinary skill in the art. This certification may then be electronically acknowledged at a user interface 114, and a signal representative of the certification may be transmitted over the network 102 and received by the server 104.

After receiving the certification, at step 352, the server 104 stores data indicative of the certification in an electronic database 106. For example, a data structure such as data structure 200 or any other suitable data structure may be stored in the electronic database 106 to track the registration status of patients.

At step 354, the server 104 authorizes the distribution of the complement inhibitor by transmitting a signal over the network 104 to the user device 110. The signal is indicative of the authorization to use the complement inhibitor in treating the registered patient. Those of ordinary skill will readily recognize that the authorization can take many forms provided that they are suitable for use with the various systems of the present invention.

Figure 4:
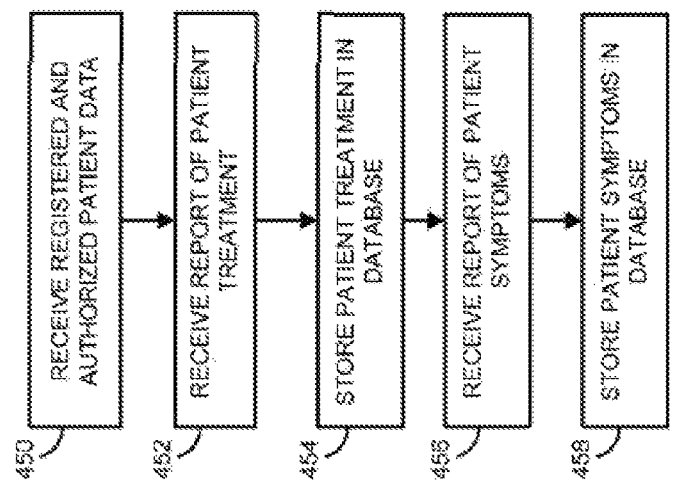
FIG. 4 is a flowchart of an exemplary method to receive and store patient-related data.

FIG. 4 is a flowchart of a method 400 that may be implemented by the server 104 to receive and store patient-related data. The method 400 includes the steps of receiving registered and authorized patient data (step 450), receiving a report of patient treatment (step 452), storing the patient treatment in a database (step 454), receiving a report of patient symptoms (step 456), and storing the patient symptoms in the database (step 458).

At step 450, the server 104 receives data related to a registered patient from a user device 110. For example, a user at the user device 110 may wish to enter patient-related data into the electronic database 106 and first provides selected data identifying the patient. The received data may include the patient's identification number, such as depicted in the first column of data structure 200, or any other suitable data identifying the patient.

At step 452, the server 104 receives an electronic report of features of a patient's treatment. The report may include information such as a drug that was administered to the patient, the time and date of administration, and an amount of the administered drug. The report may further include an identity of a person who administered the drug, where the administration took place, or any other selected information related to the treatment of the patient.

At step 454, the server 104 stores data corresponding to the received report of patient treatment in the electronic database 106. In some implementations, the processor 105 is configured to process the received report before storage. For example, the information in the received report may be sorted or categorized to facilitate efficient future retrieval of the data.

At step 456, the server 104 receives a report of patient symptoms that are determined during one or more subsequent treatment sessions or evaluations of the patient at the same or different health care facility. The report may include quantitative measures such as the patient's temperature, blood pressure, or any other suitable physiological metric used to monitor a patient's overall health. In addition, the report may also include information such as aches, inflammation, irritation, discoloration, or any other suitable symptom identified during that subsequent session. The symptom report may also include times or time intervals corresponding to each symptom.

At step 458, the patient symptoms are stored in the electronic database 106. In some implementations, the processor 105 is configured to process the received patient symptoms before storage. As an example, the information in the received patient symptom report may be processed to facilitate efficient future retrieval of the data and to efficiently group a large number of patients together who exhibit similar symptoms. In particular, a quantitative measure such as the patient's temperature may be categorized as very high, high, normal, low, or very low, for example.

Figure 5:
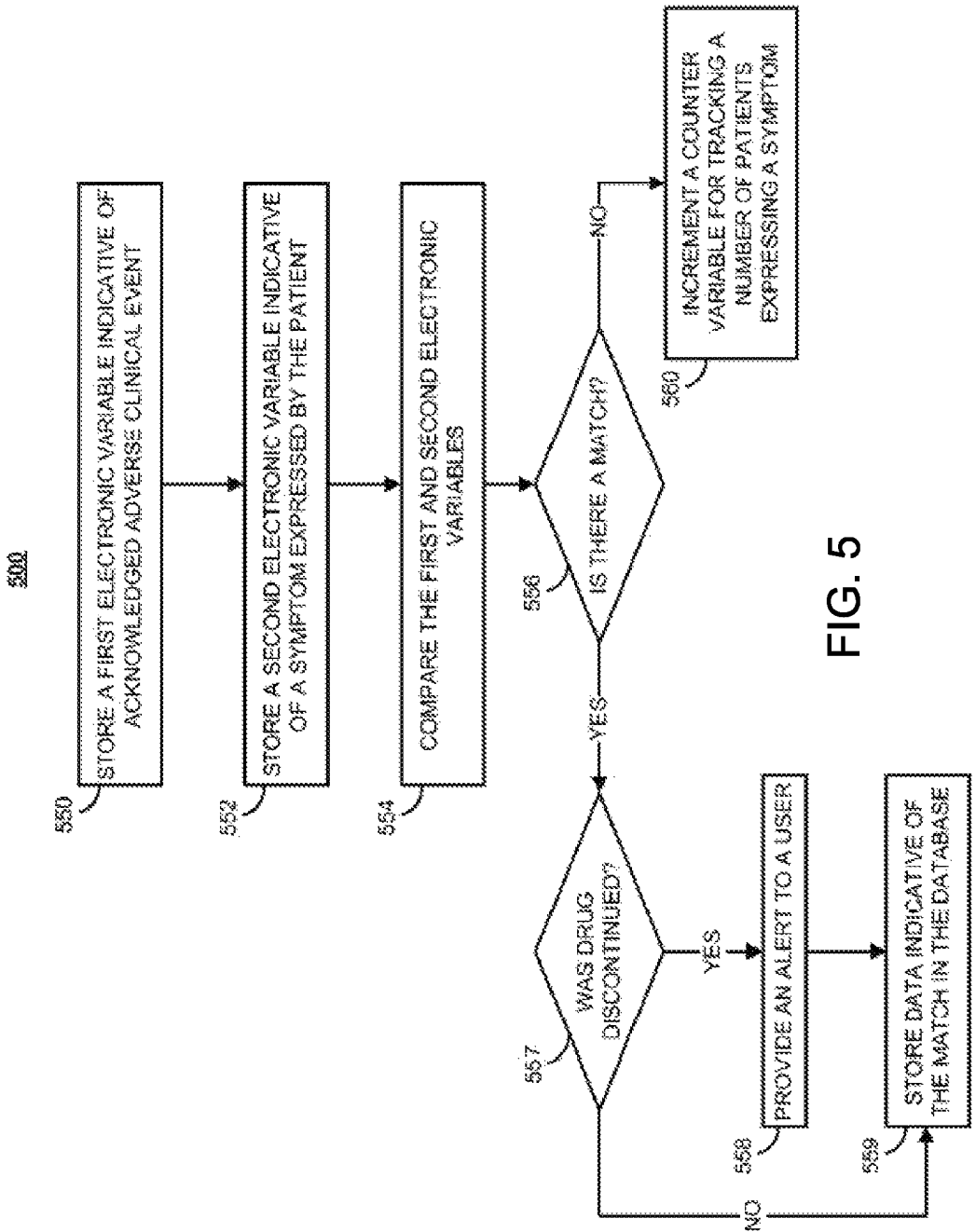
FIG. 5 is a flowchart of an exemplary method to compare a symptom expressed by a patient with an adverse clinical event.

FIG. 5 is a flowchart of a method 500 that may be implemented by the server 104 to compare a symptom expressed by a patient with an adverse clinical event, such as an adverse event corresponding to a risk certified previously by the patient or the patient's representative (e.g., FIG. 3). The method 500 includes the steps of storing a first electronic variable indicative of an acknowledged adverse clinical event (step 550) and storing a second electronic variable indicative of a symptom expressed by the patient (step 552). The first and second electronic variables are compared (step 554), and the processor 105 determines whether there is a match between the two variables (step 556). If a match is identified, then data indicative of the match is stored in the electronic database 106 (step 558), and a warning or other indicator may be provided. A counter variable may be incremented that tracks a number of patients expressing a symptom that is not included as an adverse clinical event (step 560).

At step 550, the server 104 stores a first electronic variable indicative of an adverse clinical event acknowledged by the patient's representative during patient registration. The first electronic variable may be an identification number corresponding to the clinical event, or may simply be a flag variable indicating that the adverse clinical event has been acknowledged by the patient's representative. Other types of variables suitable for use with the systems of the present invention would be obvious to one of ordinary skill in the art.

At step 552, the server 104 stores a second electronic variable indicative of a symptom expressed by the patient. The second electronic variable may be an identification number corresponding to the symptom and may have been received with the report of patient symptoms as described in relation to FIG. 4. According to one practice, the report of patient symptoms may have been processed to determine a value for the second electronic variable.

At step 554, the first and second electronic variables are compared. The processor 105 may perform some processing on one or both of the electronic variables in order to process, convert or otherwise manipulate the variables into a form suitable for comparison.

At step 556, the server 104 determines whether there is a match between the two electronic variables. In particular, a match requires that the expressed symptom corresponds to the registered adverse clinical event in some way. Furthermore, a match may be associated with a match strength value. According to one example, an adverse clinical event associated with a drug may be that the patient is susceptible to a rise in temperature by a selected amount, for example, at least 5 degrees. If the patient exhibits an increase in temperature greater than the selected amount (e.g., 6 degrees) after being administered the drug, the server 104 may associate one match strength value with the patient. If another patient exhibits an increase in temperature of 10 degrees after being administered the drug, the server 104 may associated a stronger match strength value with the other patient. These match strength values may be also be stored in the electronic database 106 when updating the patient's information. The match strength values can be pre-stored, pre-assigned or otherwise programmed in the system so that the processor can determine or calculate a proper match strength value.

When the server 104 determines that a match has occurred, at step 557, the server 104 determines whether the drug was discontinued prior to the expression of the symptom by the patient. In particular, if the drug was discontinued prior to the expression of the symptom, at step 558, the server 104 provides an alert to a user. The alert may include information indicating that a match between a risk of a side effect that was acknowledged by the patient's representative and associated with discontinuing use of the drug and a symptom expressed by the patient has occurred. At step 559, the server 104 may store data indicative of the match, such as the match strength value, or a flag variable indicating the match, in the electronic database 106 at step 558.

If the server 104 determines there is no match between the first and second electronic variables, at step 560, the server 104 may increment a counter variable. The counter variable corresponds to the expressed symptom and represents a number of registered patients that have expressed the symptom during a predefined time interval after administration of the drug. The time interval may be a minute, an hour, a day, a week, or any other suitable time interval corresponding to an expression of a symptom after drug administration. The server 104 may store counter variables for a number of various symptoms not normally associated with the drug. The server 104 may also store separate counter variables for categories of patients, sorted by their age, gender, or any other suitable category for a patient. By incrementing these counter variables, the server 104 keeps track of a number of patients expressing particular symptoms and can transmit an alert to an authorized user when the number of patients exceeds a predetermined threshold. In this way, the server 104 may detect symptoms that are often expressed by patients in a particular category, in which the symptoms were not previously associated with the drug.

Then, steps 552-560 may be repeated for each symptom retrieved from a received symptom report for comparison to an adverse clinical event. Furthermore, method 500 may be repeated for each adverse clinical event listed in the warning received by the patient's representative for comparison to each recorded symptom expressed by the patient.

Figure 6:
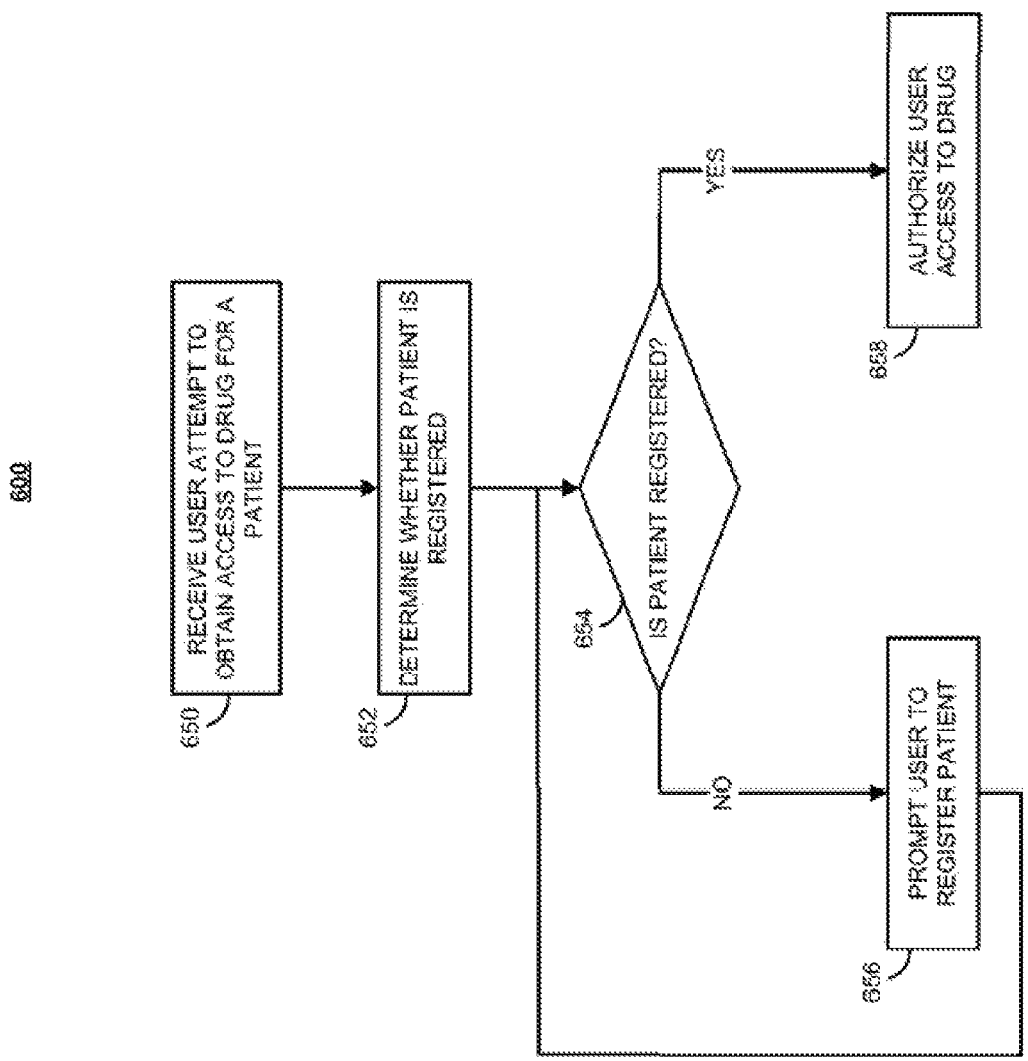
FIG. 6 is a flowchart of an exemplary method to determine whether to authorize a user access to a drug.

FIG. 6 is a flowchart of a method 600 that may be implemented by the server 104 to determine whether to authorize a user access to a selected drug (e.g., a complement inhibitor). The method 600 includes the steps of receiving a user attempt to obtain access to a drug for a patient (step 650) and determining whether the patient is registered (step 652). If the patient is registered, the server 104 authorizes the user to obtain access to the drug (step 658). Otherwise, the user is prompted to register the patient in the database (step 656). The patient may be registered by the method described in FIG. 7.

Figure 7:
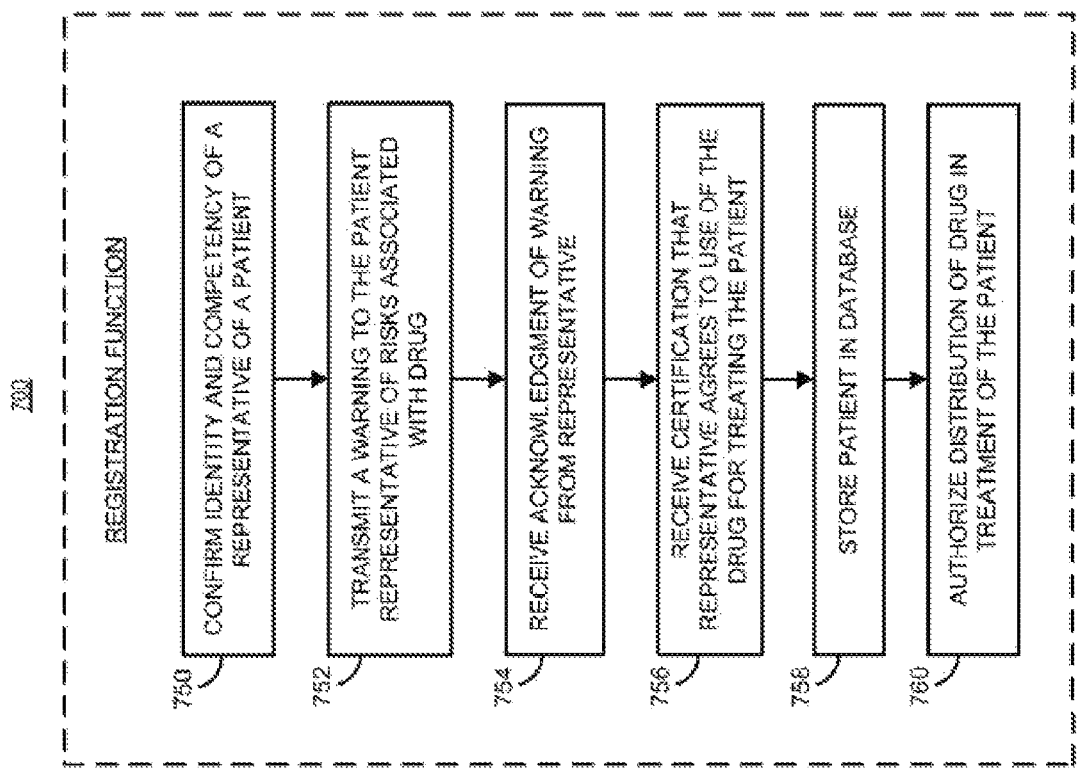
FIG. 7 is a flowchart of an exemplary method to register a patient.

FIG. 7 is a flowchart of a method 700 that may be implemented by the server 104 to register a patient. The method 700 includes the steps of confirming an identity and a competency of a representative of the patient (step 750), transmitting a warning to the patient representative of risks associated with the drug (step 752), receiving acknowledgment of the warning from the representative (step 754), receiving certification that the representative agrees to the use of the drug in treating the patient (step 756), storing the patient in the database (step 758), and authorizing the distribution of the drug for treating the patient (step 760).

Using the above-described techniques, a complement-inhibitor-based treatment may be carried out. As noted above, this complement-inhibitor-based treatment may entail an increased risk of adverse events, such as meningococcal infections. Accordingly, the complement-inhibitor-based treatment may be combined with a computer-implemented risk evaluation and mitigation strategy (REMS) and a safety and support program (SSP) to reduce the risk of adverse events and to effectively and quickly address an adverse event if one occurs.

Risk Evaluation and Mitigation Strategy (REMS)

The Risk Evaluation and Mitigation Strategy (REMS) may be used to mitigate the occurrence and morbidity associated with adverse events such as meningococcal infections, and furthermore to educate health care providers, patients, and caregivers regarding the increased risk of adverse events, the early signs of adverse events, and the need for immediate medical evaluation of signs and symptoms consistent with possible occurrences of adverse events.

The REMS may involve certifying and/or registering qualified healthcare providers that agree to abide by the REMS in a database. Prior to providing the complement inhibitor for complement-inhibitor-based treatment, the database may be consulted to determine if the health care provider is registered in the database. Registration in the database may involve receiving certification from the health care provider that the health care provider will: counsel patients and provide patient educational materials to the patient, provide a Medication Guide to the patient prior to each infusion with the complement inhibitor, review educational materials and product labeling associated with the complement inhibitor and comply with the directions for safe use, including ensuring patients receive a meningococcal vaccine, including a meningococcal vaccine to *Neisseria meningitidis* serotype B, and promptly report adverse events, such as cases of meningococcal infection, including the patients' clinical outcomes.

A provider of the complement inhibitor may consult the database to verify that a prescriber requesting the complement inhibitor is registered in the database. The provider may be prompted on a predetermined basis (e.g., once per year) to contact the prescribers in the registry in order to provide educational materials to the registered prescribers.

One important reason for implementing the REMS procedures is that early intervention in some kinds of adverse events, such as meningococcal infections, is critical to successful outcomes. However, the nature of treatment with a complement inhibitor may make it difficult to achieve early intervention.

For example, the urgency required to treat a meningococcal infection may necessitate treatment using different physicians than the original prescriber of the complement inhibitor. Given that paroxysmal nocturnal hemoglobinuria and atypical hemolytic uremic syndrome (two conditions treated by complement inhibitors, such as Soliris) are ultra-rare, the treating health care provider may not be familiar with Soliris, and the increased risk for infection in the patient, unless the patient informs the health care provider. Furthermore, patients who are familiar with the signs and symptoms of a meningococcal infection are more likely to seek out and receive early intervention which is known to lead to better outcomes.

Figure 8:
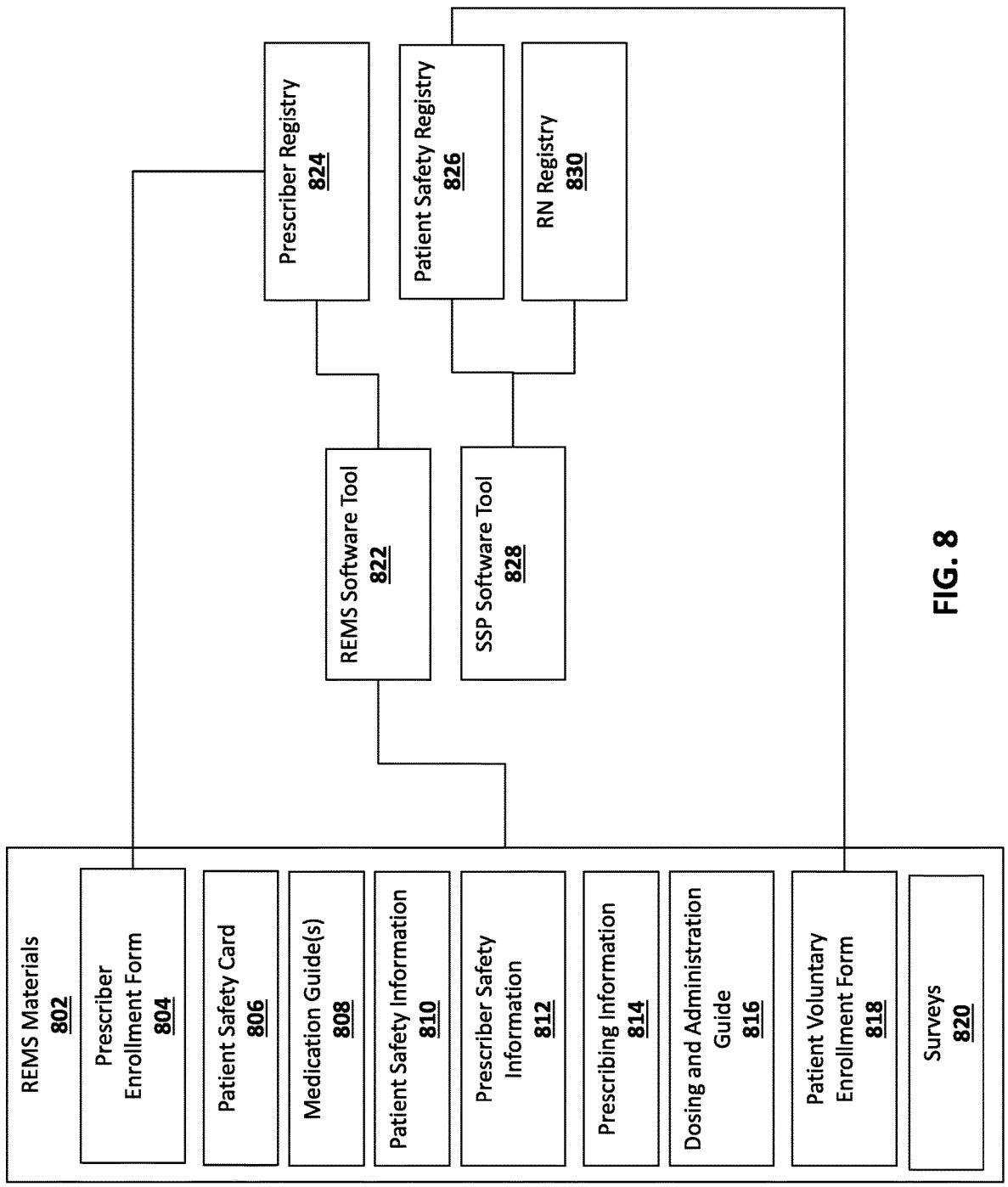
FIG. 8 depicts an exemplary system for implementing an exemplary risk evaluation and management strategy and an exemplary safety support program.

FIG. 8 depicts exemplary components for implementing the REMS. The REMS may make use of REMS Materials 802, which may include materials to be distributed to patients and prescribers.

The REMS materials 802 may include a prescriber enrollment form 804. The prescriber enrollment form 804 may be used to enroll prescribers in the REMS. In some embodiments, prescribers may submit a prescriber enrollment form 804 to a provider of a complement inhibitor prior to ordering the complement inhibitor from the provider. Alternatively or in addition, the prescriber may attempt to order the complement inhibitor, and the provider may inform the prescriber that the prescriber must agree to enroll in the REMS program as a condition of the drug being shipped. The prescriber enrollment form may be completed via telephone, facsimile, Internet, mail, electronic mail, or in person.

Prescribers of the complement inhibitor may be specially certified through the prescriber enrollment form 804. Certification may be based on a prescriber agreement to counsel patients and provide to patients with educational materials (listed below), to review these materials and comply with directions for safe use, and to promptly report to the complement inhibitor provider and/or FDA serious life-threatening cases of adverse events, including meningococcal infections, and the outcomes of the adverse events. Prescribers may complete the prescriber enrollment form 804 to attest to this agreement.

The prescriber enrollment form 804 may include an agreement that the prescriber will undertake one or more selected actions. These actions include a review of the product labeling and educational materials. These include a review of the Patient Safety Card 806, the Medication Guide 808, the Patient Safety Information 810, the Prescriber Safety Information 812, the Prescribing Information 814, and the Dosing and Administration Guide 816. The prescriber may also be required to perform additional actions, such as comply with safety instructions for use including ensuring patients are vaccinated with meningococcal vaccination, including meningococcal vaccination for *Neisseria meningitidis* serotype B; counsel patients and provide educational materials to the patient; agree to promptly report cases of meningococcal infections and patient outcomes; and revaccinate according to current Advisory Committee on Immunization Practices medical guidelines for vaccine use.

The Patient Safety Card 806 may also include directions for a treating physician (who may or may not be the physician that originally prescribed the complement inhibitor), which calls to the physician's attention the increased risk for the adverse event. The Patient Safety Card 806 may include an instruction for the patient to carry the card at all times, and to show the card to a treating physician upon the occurrence of an adverse event.

A Medication Guide 808 may also be provided to patients. The Medication Guide 808 may be a brief educational document providing answers to patient questions about the complement inhibitor, possible side effects and adverse events, and how and when the patient will receive the complement inhibitor. The Medication Guide 808 may include information required to be communicated to a patient (e.g., by a regulatory agency such as the FDA).

The Medication Guide 808 may be packaged with every dose of the complement inhibitor. Furthermore, the Medication Guide 808 may be provided to all prescribers for initial training along with other educational material. Through the REMS enrollment process, each prescriber may be asked to agree to dispense the Medication Guide 808 to each patient at each infusion.

The REMS materials 802 may also include Patient Safety Information 810. The Patient Safety Information 810 represents educational materials designed to be provided to the patient by the prescriber. The Patient Safety Information 810 may explain the information in the Medication Guide 808 and may explain how to use the Patient Safety Card 806. Because the Medication Guide 808 may include regulatory information, a patient may better understand the information from the Medication Guide 808 through the use of separate Patient Safety Information 810.

Particularly in the case of meningococcal infections, patient education (in addition to prescriber education) may be especially important. The Patient Safety Card 806, Medication Guide 808, and Patient Safety Information 810 each provide opportunities to educate the patient and reinforce their understanding of the risk of adverse events.

One advantage of patient education through the combination of the Patient Safety Card 806, Medication Guide 808, and Patient Safety Information 810 is that the chance of early intervention in the case of an adverse event is increased. Early intervention in the case of meningococcal infections is especially critical to successful outcomes. The urgency required to treat a meningococcal infection may necessitate treatment using different physicians. Given that paroxysmal nocturnal hemoglobinuria and atypical hemolytic uremic syndrome (two conditions treated by complement inhibitors, such as Soliris) are ultra-rare, the treating health care provider may not be familiar with Soliris, and the increased risk for infection in the patient, unless the patient informs the health care provider. Furthermore, patients who are familiar with the signs and symptoms of a meningococcal infection are more likely to seek out and receive early intervention which is known to lead to better outcomes.

The REMS materials 802 may further include Prescribing Safety Information 812. The Prescribing Safety Information may include an explanation to a prescriber as to how to explain the Patient Safety Card 806 and the Mediation Guide 808 to patients. By providing multiple different sources of consistent information (e.g., the Medication Guide 808 from the complement inhibitor provider and the Prescribing Safety Information 812 from the prescriber), the patient's understanding of the safety information contained in the REMS materials 802 may be increased.

The REMS materials 802 may further include Prescribing Information 814. The Prescribing Information 814 may provide, for the prescriber, a detailed overview of the complement inhibitor, conditions treated by the complement inhibitor, mechanisms of action, warnings and precautions, possible adverse events associated with the complement inhibitor, and other information needed to prescribe and use the complement inhibitor safely and effectively. The Prescribing Information 814 may include information required by regulatory agencies, such as the FDA.

A Dosing and Administration Guide 816 may also be provided. The Dosing and Administration Guide 816 may serve as a reference for the prescriber as to how to properly administer the complement inhibitor to a patient.

The REMS materials may also include a Patient Voluntary Enrollment Form 818. The Patient Voluntary Enrollment Form 818 may allow a patient to enroll, if desired, in the Safety and Support Program (SSP). The Patient Voluntary Enrollment Form 818 may provide patients with ways to discuss the educational material with a Nurse Case Manager through the SSP. The patient may be given the opportunity to ask any questions that he/she may have and to enroll in the SSP program. Enrolling in the SSP program provides an extra point of contact with the patient (in this case, between the patient and the provider of the complement inhibitor) in order to further reinforce the patient's understanding of the possibility of adverse events.

The REMS materials 802 may optionally include Surveys 820. In some embodiments, a provider of the complement inhibitor may conduct surveys of prescribers and/or patients at predetermined intervals (e.g., every two years). The Surveys 820 may be used to assess prescriber and patient understanding of the REMS educational materials which communicate important safety information associated with complement-inhibitor-based treatment and meningococcal infection risk, as well as steps that can be taken to minimize the risks. In the Surveys 820, participants may be asked to indicate which educational materials have been read or referenced over the survey period and how recently the survey participant consulted these materials over the past year.

When the survey 820 is directed to a prescriber, the survey may contain a series of questions to gauge understanding of the key REMS concepts, including but not limited to the risk of meningococcal infection; the need for meningococcal vaccinations and revaccinations, including meningococcal vaccination for *Neisseria meningitidis* serotype B; the need to educate patients regarding the use of the Patient Safety Card 806: the need for continuous reinforcement of the risks associated with complement-inhibitor-based treatment; and/or what to do in the event of an infection.

When the survey 820 is directed to a patient, the survey may contain a series of questions to gauge his/her understanding of the key REMS concepts, including but not limited to the risk of meningococcal infection; the need for meningococcal vaccinations and revaccinations, including meningococcal vaccination for *Neisseria meningitidis* serotype B; the use of the Patient Safety Card 806; the warning signs of a meningococcal infection; and/or what to do in the event of infection.

A REMS Software Tool 822 may enforce protocols of the REMS, ensure ongoing prescriber and patient education, and assist in the detection and reporting of adverse events. The REMS software tool 822 may be programmed with the dates, time intervals, and actions to be taken in accordance with the REMS. Exemplary procedures that may be carried out by the REMS Software Tool 822 are described in more detail with respect to FIG. 9A and FIG. 9B.

To ensure that the complement inhibitor is distributed only to certified prescribers, the REMS Software Tool 822 may maintain a database of certified prescribers in the REMS program. Additionally, the REMS Software Tool 822 may generate regular prompts to verify that prescribers comply with requirements of the REMS Program.

Safety Support Program

A Safety Support Program (SSP) may complement and reinforce the REMS. The SSP provides education as well as disease and treatment support for patients who have been enrolled in a complement-inhibitor-based treatment plan. The SSP provides additional procedures beyond those defined in the REMS to further mitigate the risk of serious meningococcal infection in patients being treated with complement inhibitors. The SSP concentrates on counseling the patient, training (e.g., need for vaccination; risks of developing meningococcal and other serious infections; and the risk of developing serious hemolysis following complement inhibitor discontinuation with continued monitoring after discontinuation), enrollment, documentation, and safety evaluation. Examples of activities performed in the SSP include: each patient may be assigned a professional nurse personal contact to serve as their Nurse Case Manager; calls made at predetermined periods of time (e.g., monthly) to patients by the Nurse Case Managers as allowed by the patient to ensure that they have a copy of the Patient Safety Card 804 and to review signs and symptoms of meningococcal infection; patient vaccination dates are monitored and a revaccination reminder letter is mailed to the prescriber or patient in advance of each patient's 3-year vaccination anniversary date; patients are encouraged to voluntarily report adverse events to their Nurse Case Manager; and patients are encouraged to contact their Nurse Case Manager with any questions about their treatment.

With reference again to FIG. 8, a patient safety registry 826 may be maintained as part of the SPP. The patient safety registry may include patients who have voluntarily signed up for the SPP and who wish to receive reminders and educational materials regarding treatment with the complement inhibitor. Patients may be enrolled in the SSP and may be entered into the patient safety registry upon receipt of the patient voluntary enrollment form 818 from the REMS materials 802.

A Baseline Data Form may be completed for each voluntarily enrolled patient in the patient safety registry 826 within 30 days of initiating complement-inhibitor-based treatment. The Baseline Data Form may be used to collect information regarding patient demographics, past medical history and current medical condition, and vaccination status.

An SSP software tool 828 may enforce protocols of the SSP, for example, by prompting a Registered Nurse Care Manager assigned to a patient to perform one or more of the above-identified actions. The SSP software tool 828 may be programmed with the dates, time intervals, and actions to be taken in accordance with the SSP. Exemplary procedures that may be carried out by the SSP Software Tool 828 are depicted in FIG. 9B and FIG. 9C.

The SSP may be staffed by Registered Nurse Case Managers who can address questions related to disease and treatment, perform a consultation at any time, and provide tools that help patients track and manage their disease. It is very important to realize that a meningococcal infection is an acute disease and can progress to death or permanent disability within a day. The availability of a Nurse Case Manager is particularly useful because the symptoms of early meningococcal infection are diverse and not every patient has the same set of presenting symptoms. In addition, the symptoms are not unique to meningococcal infection and may seem like flu, gastroenteritis or even a hangover. Symptoms include fever, cold hands and feet, sore muscles, sore joints, nausea, vomiting, stiff neck, painful neck, backache, sore throat, lack of energy and different combinations of symptoms may present during a given episode. When a patient who is participating in a patient safety support program experiences any sort of symptom, they may call their Nurse Case Manager who understands the diversity of possible symptoms may direct them to immediately seek treatment for possible meningococcal infection in the form of antibiotics.

Nurse Case Managers also put patients in touch with other patients suffering from the same conditions when requested to do so. To this end, the SSP software tool may access a registered nurse registry 830, which may be a database identifying registered nurses who have agreed to participate in the SSP. In some embodiments, all activities of the SSP may be performed by a Registered Nurse Case Manager.

Exemplary procedures performed by the REMS software tool 822 and the SPP software tool 828 are next described with reference to FIGS. 9A-9C.

Exemplary Method for Implementing REMS and SSP

Figure 9A:
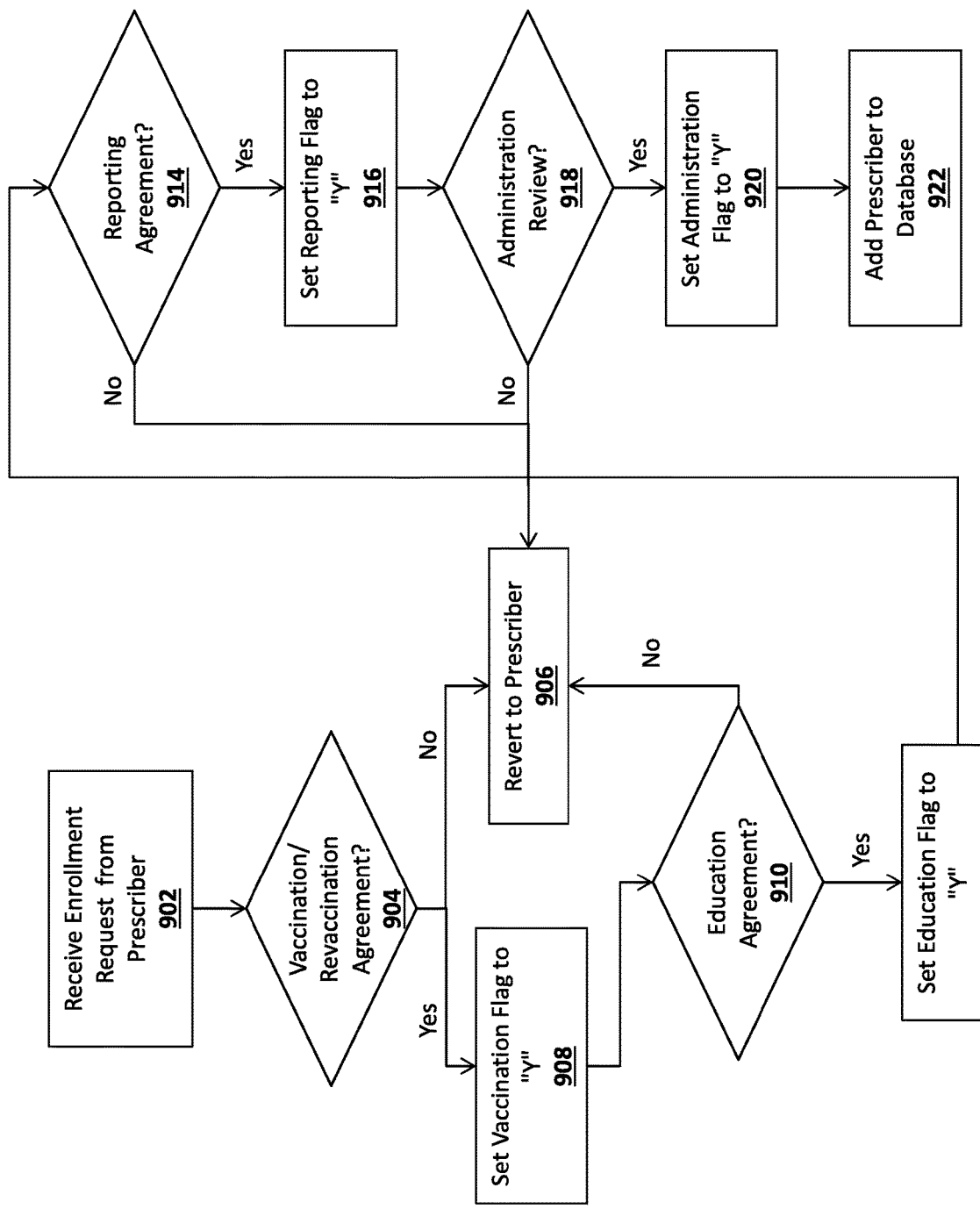
FIG. 9A, FIG. 9B, and FIG. 9C are flowcharts depicting exemplary methods for implementing a risk evaluation and management strategy and a safety support program.
Figure 9B:
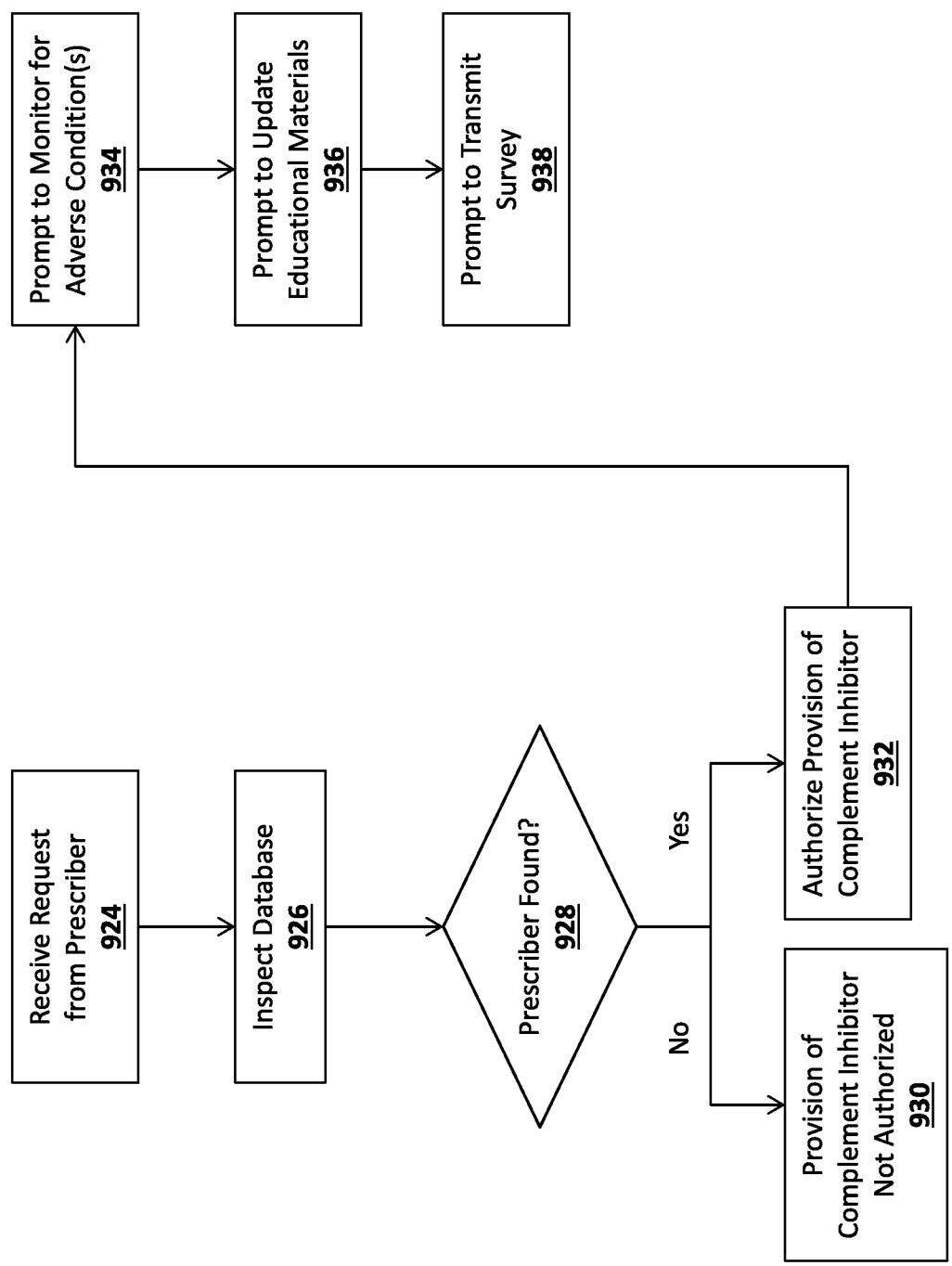
Figure 9C:
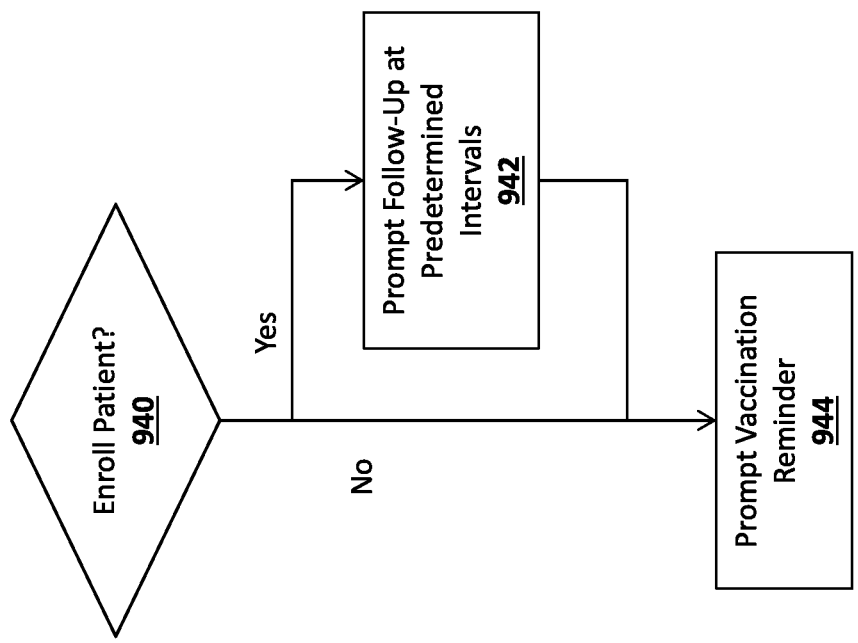

FIG. 9A depicts an exemplary procedure for enrolling a prescriber in the REMS. At step 902, a provider of a complement inhibitor may receive an enrollment request from a prescriber or other health care professional (HCP). The enrollment request may request that the provider enroll the prescriber/HCP in the REMS/SSP program. The enrollment request may optionally request that the provider send the complement inhibitor to the prescriber. The enrollment request may be in the form, for example, of the Prescriber Enrollment Form 804. The enrollment request may be electronically submitted, in which case it may be received and processed by the REMS software tool 822. If the enrollment request is not electronically submitted (e.g., the enrollment request is submitted by phone, mail, or in person), then information from the enrollment request may be entered into the REMS software tool 822 by the recipient of the enrollment request.

The REMS software tool 822 may create an entry associated with the requesting prescriber/HCP. For example, the REMS software tool 822 may create a new entry in the Prescriber Registry 824, or may temporarily store information about the requesting prescriber/HCP in memory until it has been verified that the prescriber/HCP has agreed to abide by all of the requirements of the REMS and/or SSP.

At step 904, it may be determined whether the requester has agreed to vaccination and/or revaccination requirements for the complement inhibitor. For example, the Prescriber Enrollment Form 804 may include a requirement that the prescriber/HCP agrees to vaccinate (or have vaccinated) any patients receiving the complement inhibitor according to a predetermined time requirement (e.g., vaccination must occur at least two weeks prior to administering the complement inhibitor). The Prescriber Enrollment Form 804 may also require that the prescriber/HCP agrees to revaccinate the patient at predetermined intervals (e.g., every three years for a meningococcal vaccination) and/or agrees to educate the patient regarding the ongoing need for revaccination. The prescriber may indicate their agreement to the vaccination/revaccination requirements (or any other requirement) through an initial or checkmark on a vaccination-specific portion of the Prescriber Enrollment Form 804, by signing a general agreement to abide by all of the requirements on the Prescriber Enrollment Form 804, through an oral agreement, or through other means showing an active, affirmative agreement to abide by the vaccination/revaccination requirements.

If the answer at step 904 is "NO" (i.e., the prescriber has not agreed to the vaccination/revaccination requirements), then the REMS software tool 822 may, at step 906, set a vaccination flag associated with the prescriber entry created in step 902 to "NO" or "FALSE." The REMS software tool 822 may indicate that the prescriber/HCP cannot be certified in the Prescriber Registry 824 until the prescriber/HCP has agreed to the vaccination/revaccination requirements, and may flag the prescriber/HCP for follow up by the provider of the complement inhibitor. If the answer at step 904 is "YES," then at step 908 the REMS software tool 822 may set the vaccination flag to "YES" or "TRUE."

Additional requirements of the REMS/SSP are addressed in steps 910, 914, and 918. Optionally, even if the answer at step 904 is "NO," processing may continue to steps 910, 914, and 918 so that each missing requirement can be flagged to the prescriber/HCP at the same time. If the enrollment request was received electronically at step 902, the REMS software tool 822 may automatically respond to the request by transmitting an indication of any or all missing requirements to the prescriber/HCP.

At step 910, it may be determined whether the requester has agreed to education requirements for the complement inhibitor. For example, the Prescriber Enrollment Form 804 may include a requirement that the prescriber/HCP agrees to counsel patients, caregivers, and/or legal guardians and provide educational materials to the patients, caregivers, or legal guardians. Such educational materials may include the Patient Safety Card 806 and/or the Medication Guide 808. If the answer at step 910 is "NO" (i.e., the prescriber has not agreed to the education requirements), then the REMS software tool 822 may set an education flag associated with the prescriber entry created at step 902 to "NO" or "FALSE." The REMS software tool 822 may indicate that the prescriber/HCP cannot be certified in the Prescriber Registry 824 until the prescriber/HCP has agreed to the education requirements, and may return to step 906 to flag the prescriber/HCP for follow up by the provider of the complement inhibitor. If the answer at step 910 is "YES," then at step 912 the REMS software tool 822 may set the education flag to "YES" or "TRUE."

At step 914, it may be determined whether the requester has agreed to reporting requirements relating to adverse events associated with the complement inhibitor. For example, the Prescriber Enrollment Form 804 may include a requirement that the prescriber/HCP agrees to promptly report cases of specified adverse events (such as meningococcal infections, other infections caused by encapsulated bacteria, generally infections, and hemolysis) to the provider and/or a regulatory agency such as the FDA. If the answer at step 914 is "NO" (i.e., the prescriber has not agreed to the reporting requirements), then the REMS software tool 822 may set a reporting flag associated with the prescriber entry created at step 902 to "NO" or "FALSE." The REMS software tool 822 may indicate that the prescriber/HCP cannot be certified in the Prescriber Registry 824 until the prescriber/HCP has agreed to the reporting requirements, and may return to step 906 to flag the prescriber/HCP for follow up by the provider of the complement inhibitor. If the answer at step 914 is "YES," then at step 916 the REMS software tool 822 may set the reporting flag to "YES" or "TRUE."

At step 918, it may be determined whether the requester has agreed to administration requirements relating to adverse events associated with the complement inhibitor. For example, the Prescriber Enrollment Form 804 may include a requirement that the prescriber/HCP agrees to review product labeling and prescriber educational materials (such as any or all of the Prescriber Safety Information 812, Prescribing Information 814, and Dosing and Administration Guide 816), and to administer the complement inhibitor in accordance with the product labeling and the prescriber educational materials. If the answer at step 918 is "NO" (i.e., the prescriber has not agreed to the administration requirements), then the REMS software tool 822 may set a reporting flag associated with the prescriber entry created at step 902 to "NO" or "FALSE." The REMS software tool 822 may indicate that the prescriber/HCP cannot be certified in the Prescriber Registry 824 until the prescriber/HCP has agreed to the administration requirements, and may return to step 906 to flag the prescriber/HCP for follow up by the provider of the complement inhibitor. If the answer at step 918 is "YES," then at step 920 the REMS software tool 822 may set the administration flag to "YES" or "TRUE."

At step 922, the REMS software tool 822 may determine if each of the flags (vaccination, education, reporting, and administration) have been set to "YES" or "TRUE." If the prescriber/HCP has agreed to each of these requirements, then the REMS software tool 822 may add the prescriber/HCP to the Prescriber Registry 824. At that point, the prescriber may be considered as certified to prescribe the complement inhibitor.

It is noted that the procedure depicted in FIG. 9A is exemplary only. For example, the vaccination flag, the education flag, the reporting flag, and the administration flag may all be combined into one flag (e.g., a single flag indicating that the prescriber has agreed to all relevant conditions). Alternatively, these flags may be implicit in the entry of a prescriber into the prescriber database (i.e., if a prescriber is present in the database, this may be taken to mean that the prescriber has agreed to all relevant conditions).

FIG. 9B depicts an exemplary procedure for issuing a complement inhibitor to a requesting prescriber and following up with the requesting prescriber according to the REMS/SSP. At step 924, a provider of a complement inhibitor may receive a requisition request from a prescriber/HCP. The requisition request may request that the provider send a specified number of vials or doses to the prescriber/HCP. The requisition request may be electronically submitted, in which case it may be received and processed by the REMS software tool 822. If the requisition request is not electronically submitted (e.g., the requisition request is submitted by phone, mail, or in person), then information from the requisite request may be entered into the REMS software tool 822 by the recipient of the requisition request.

At step 926, the REMS software tool 822 may be used to inspect the Prescriber Registry 824. The REMS software tool 822 may access the Prescriber Registry 824, either locally (e.g., by consulting a database stored in memory on the same machine as the REMS software tool 822) or remotely (e.g., by using a network connection and/or remote database procedure calls to retrieve information from a database stored on a machine remote from the REMS software tool 822).

At step 928, the REMS software tool 822 may determine whether the prescriber/HCP was located in the Prescriber Registry 824. In some embodiments, the presence of the prescriber/HCP in the Prescriber Registry 824 may be sufficient to indicate that the prescriber is certified to provide the complement inhibitor. In other embodiments, if the Prescriber Registry 824 includes flags (such as the above-described vaccination flag, education flag, reporting flag, and administration flag) or other indicia of suitability for receiving the complement inhibitor, the REMS software tool 822 may verify that all or a sufficient number (as may be determined based on the application) of flags or indicia are set to appropriate values in order to certify the prescriber/HCP. If the answer at step 928 is "NO," then the prescriber/HCP is not certified to provide the complement inhibitor. Accordingly, at step 930, the REMS software tool 822 may report that the prescriber/HCP is not authorized to receive the complement inhibitor. Optionally, the REMS software tool 822 may automatically transmit a message describing any requirements not met by the prescriber/HCP, and including some or all of the REMS materials 802. If the answer at step 928 is "YES," then at step 932 the REMS software tool 822 may authorize sending the complement inhibitor to the prescriber/HCP. The REMS software tool 822 may add one or more follow-up dates to the prescriber/HCP's entry in the Prescriber Registry 824. For example, the follow-up dates may include dates on which the prescriber/HCP should be contacted to determine whether the prescriber/HCP is aware of any adverse conditions that have not yet been reported to the provider, dates on which the prescriber/HCP should be provided with additional or new copies of educational materials, and dates on which the prescriber/HCP and/or the prescriber/HCP's patient should be provided with surveys.

At step 934, when the REMS software tool 822 identifies that an adverse-condition follow up date has arrived, the REMS software tool 822 may prompt the provider to contact the prescriber/HCP to determine whether any unreported adverse events have occurred. The follow-up of step 934 may occur at predetermined times or intervals, such as on a monthly or annual basis, or after a predetermined amount of time after the prescriber requests the complement inhibitor. Any adverse events including adverse events originally reported by the prescriber/HCP and adverse events discovered during the follow-up of step 934 may be tracked in the REMS software tool 822 for completeness and to monitor outcome, especially serious infections, using a standard data gathering approach to identify the likely cause of the infection and other features of the adverse event. One or more attempts may be made by the provider to obtain follow-up information. The REMS software tool 822 may generate and present individual meningococcal reports and may conduct a monthly and/or quarterly signal detection process which reviews adverse events reported worldwide. One possibility at step 934 (among other steps in FIGS. 9A-9C) is that the prescriber may indicate that the patient has been "lost to follow up" (i.e. the prescriber has not followed up with the patient due to for example an inability to locate the patient). Due diligence may be performed to follow-up patients reported by the HCP as lost to follow up. If the patient is eventually contacted and it is discovered that the patient has switched to a different HCP, the patient's new prescriber may be checked against the prescriber database to verify if the current prescriber is enrolled in the REMS/SSP program. If not, the provider may send the REMS materials 802 to the new prescriber and request that the prescriber enroll in the REMS/SSP program. Alternatively, if the patient indicates that treatment has been discontinued, the last date of complement inhibitor treatment may be entered into the Patient Safety Registry 826, as well as information provided by the prescriber/HCP related to follow-up after complement inhibitor discontinuation.

At step 936, when the REMS software tool 822 identifies that an education material update date has arrived, the REMS software tool 822 may prompt the provider to contact the prescriber/HCP to provide the prescriber/HCP with updated copies of the REMS materials 802, if any of the materials have been updated, and/or copies of documents such as the Prescriber Safety Information 812, the Prescribing Information 814, and the Dosing and Administration Guide 816. The follow-up of step 936 may occur at predetermined times or intervals, such as on an annual basis, or after a predetermined amount of time after the prescriber requests the complement inhibitor, or at any time in which the educational materials are updated. The purpose of this outreach is to remind prescribers of the REMS program and emphasize the need for safe use of complement inhibitors. The REMS software tool 822 may prompt the provider to review and discuss with the prescribers the educational material previously provided and update them on any new data available to the provider.

At step 938, the provider of the complement inhibitor may be prompted, on a predetermined basis, to send surveys 820 to the prescribers in the Prescriber Registry 824 and/or patients in the Patient Safety Registry 826. The surveys may assess compliance with vaccination requirements as well as knowledge of the risks of complement inhibitor treatment and the need for vaccination. In addition to providing information to the provider regarding patient and prescriber compliance with the REMS/SSP requirements, the surveys 820 provide an additional opportunity to reinforce the requirements and present them to the prescriber/patient in a different format.

FIG. 9C depicts an exemplary procedure for enrolling a patient in the SSP. At step 940, the SPP software tool 828 may decide whether to enroll a patient in the SPP. For example, the SPP software tool 828 may enroll a patient in the SPP upon receiving an enrollment request, such as the Patient Voluntary Enrollment Form 818. The enrollment request may be electronically submitted, in which case it may be received and processed by the SPP software tool 828. If the enrollment request is not electronically submitted (e.g., the enrollment request is submitted by phone, mail, or in person), then information from the enrollment request may be entered into the SPP software tool 828 by the recipient of the enrollment request.

Upon receiving the enrollment request, the SPP software tool 828 may add information from the Patient Voluntary Enrollment Form 818 to the Patient Safety Registry 826. The information may be contained on the Patient Voluntary Enrollment Form 818, or may be contained in a subsequently-received document (e.g., the Baseline Data Form mentioned above). If the SPP software tool 828 determines that the patient's records are incomplete (e.g., if some of the patient's demographic data and/or dates of vaccination are not present), the SPP software tool 828 may request additional information from the patient (e.g., by automatically transmitting the Baseline Data Form to the patient, or by prompting the provider to do so).

If the answer at step 940 is "YES" (i.e., the patient should be enrolled in the SPP), then at step 942 the provider may be prompted on a predetermined basis (e.g., after a predetermined amount of time following an event, such as the start of treatment, the stoppage of treatment, or the occurrence of an adverse event) to follow up with the patients in the Patient Safety Registry 828. The Patient Safety Registry 828 may further be analyzed at predetermined intervals in order to determine patients at an increased risk of adverse events. Such patients may be flagged for further follow-up. The follow-ups may involve data collection beyond routine pharmacovigilance, including monitoring for early signs of meningococcal infection or other adverse events coupled with immediate evaluation of suspected infection followed by antibiotic treatment if necessary. Furthermore, the follow-ups may involve a special pharmacovigilance effort to actively monitor and collect long-term patient data pertinent to treatment with the complement inhibitor and known adverse events related to the complement inhibitor.

Regardless of whether the patient is enrolled in the SPP at step 940, at step 944, the SPP software tool 828 may prompt the provider to provide a vaccination reminder 944. If the patient was enrolled in the SPP at step 940, then the SPP software tool 828 may access the Patient Safety Registry 826 to identify the most recent date of vaccination for the client. The SPP software tool 828 may then calculate, based on a recommended amount of time between vaccinations, when to send a revaccination reminder to the patient (or when to prompt the provider to send the revaccination reminder). For example, the SPP software tool 828 may send the reminder (or prompt for the reminder to be sent) by a predetermined amount of time (e.g., two months) before revaccination is due. If the patient was not enrolled in the SPP at step 940, then the SPP software tool 828 may send revaccination reminders to prescribers/HCPs at predetermined times. The predetermined times may be a predetermined amount of time after the prescriber/HCP reports that a vaccination or complement-inhibitor treatment was first administered, or may be a general reminder to have their patients revaccinated issued at predetermined intervals (e.g., once per year).

Figure 10:
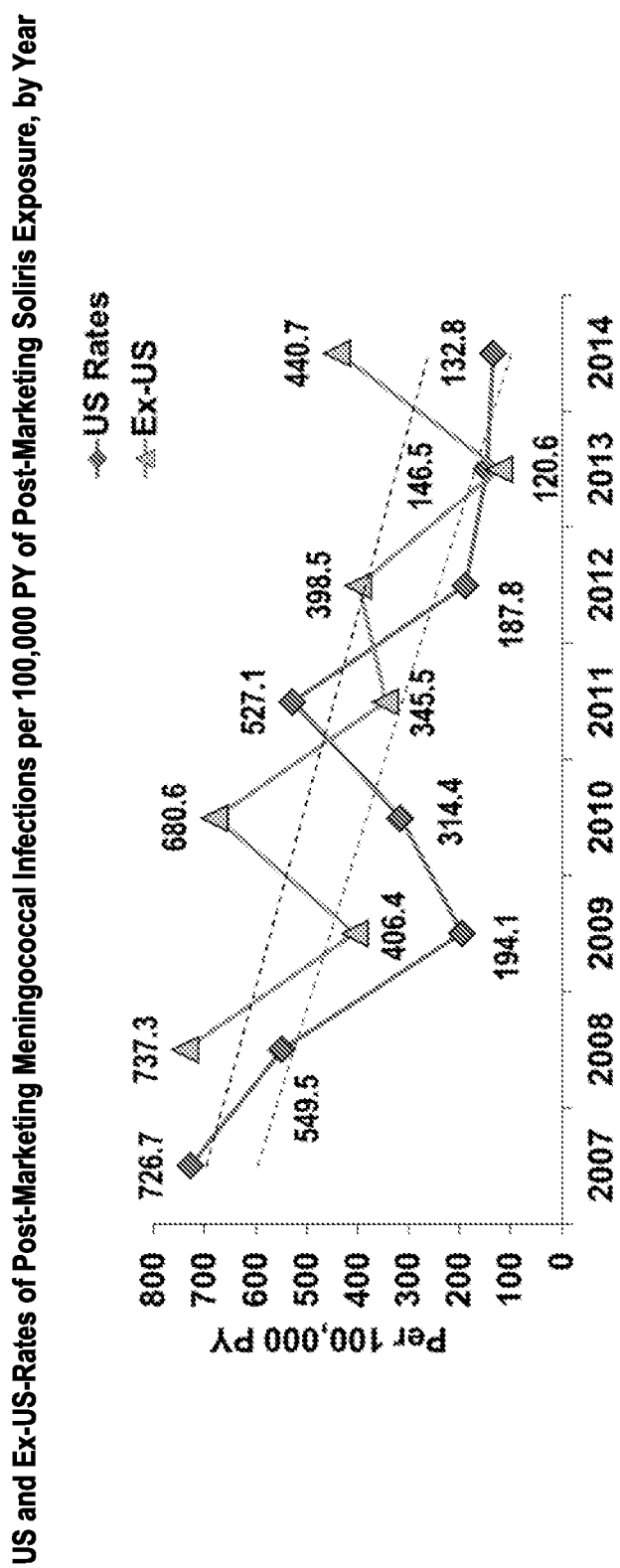
FIG. 10 is a graph depicting a reduction in meningococcal infections following the implementation of an exemplary embodiment described herein.

A REMS and SSP plan was carried out according to the above-described embodiments from 2007-2014. FIG. 10 is a graph showing rates of post-marketing meningococcal infections per 100,000 persons, by year, for patients exposed to a C5 complement inhibitor (Soliris®) following FDA approval of the complement inhibitor. As can be seen in the graph of FIG. 10, the rate of meningococcal infections showed a strong downward trend in the years following the implementation of the REMS/SSP (the sharp increase in the Ex-US rate observed in 2014 is attributed to the launch of Soliris® in new countries such as Greece). The meningococcal infection rate reported in patients with PNH immediately following market approval of Soliris was consistent with expectations based on the medical literature available for infection rates in individuals with known terminal complement mutations. Since full implementation of the REMS, a steady trend of a decreasing post-marketing meningococcal infection rate over time has been observed. Furthermore, US rates are lower compared to Ex-US rates, and the inventors believe that the REMS program is an important reason for this difference. All together, this data supports the success of the REMS in meeting its primary goal of mitigating the occurrence and morbidity associated with meningococcal infections.

Since the FDA's approval in 2007 of Soliris for the treatment of patients with PNH, a total of 15 post-marketing cases of meningococcal infections have been reported corresponding to a rate of 268.1 cases per 100,000 person years. Vaccination history was confirmed in all reported cases. Of the 15 cases, there was only 1 fatality. One reported case of invasive meningococcal infection is resolving; all remaining cases have resolved.

The rate of mortality from meningococcal infection in the general U.S. population was 2 per 15 cases (CDC 2013). The lower rate (1 per 15 cases) observed in the Soliris-treated post-marketing population strongly demonstrates the effectiveness of the REMS program, with the support of the SSP, despite the fact that Soliris-treated patients represent a sicker population than the general population. By the nature of their disease, patients with PNH and aHUS (two conditions treated by Soliris) might be expected to be at a higher risk for meningococcal infections, but the data indicates that patients receiving Soliris have a lower risk of meningococcal infection compared with individuals with LCCD. The annual number of reported post-marketing cases in Soliris-treated patients with PNH or aHUS has consistently been between 1-2, with the exception of 4 cases reported in 2011 (all in patients with PNH), despite an increase in exposure over time as more patients come on treatment or remain on treatment.

The inventors believe that this trend is attributable to the REMS program and the reinforcement of key safety messages provided by the SSP. Among other factors, strong patient knowledge regarding the need for meningococcal vaccinations and actions to take if symptoms suggest the possibility of meningococcal infection plays a significant role in mitigating the risk of meningococcal infection and its outcomes. Through the prescriber and patient education components of the REMS, and the additional activities of the SSP, these patients are in regular contact with a Nurse Case Manager and receive ongoing reinforcement of the safety messages related to Soliris treatment. The survey data available from these patients supports and illustrates the success and effectiveness of the REMS tools in educating patients. Further, the available evidence supports and illustrates the success of the REMS and SSP programs to prevent the occurrence of meningococcal infection in this at-risk population through the consistent education of both HCPs and their patients.

Those of ordinary skill in the art will readily recognize that one or more of the foregoing notifications, prompts, actions, dissemination of surveys, and the like can be performed automatically by one or more of the computer device or processor and/or by the one or more of the REMS software tool 822 and the SSP software tool 828.

Figure 11:
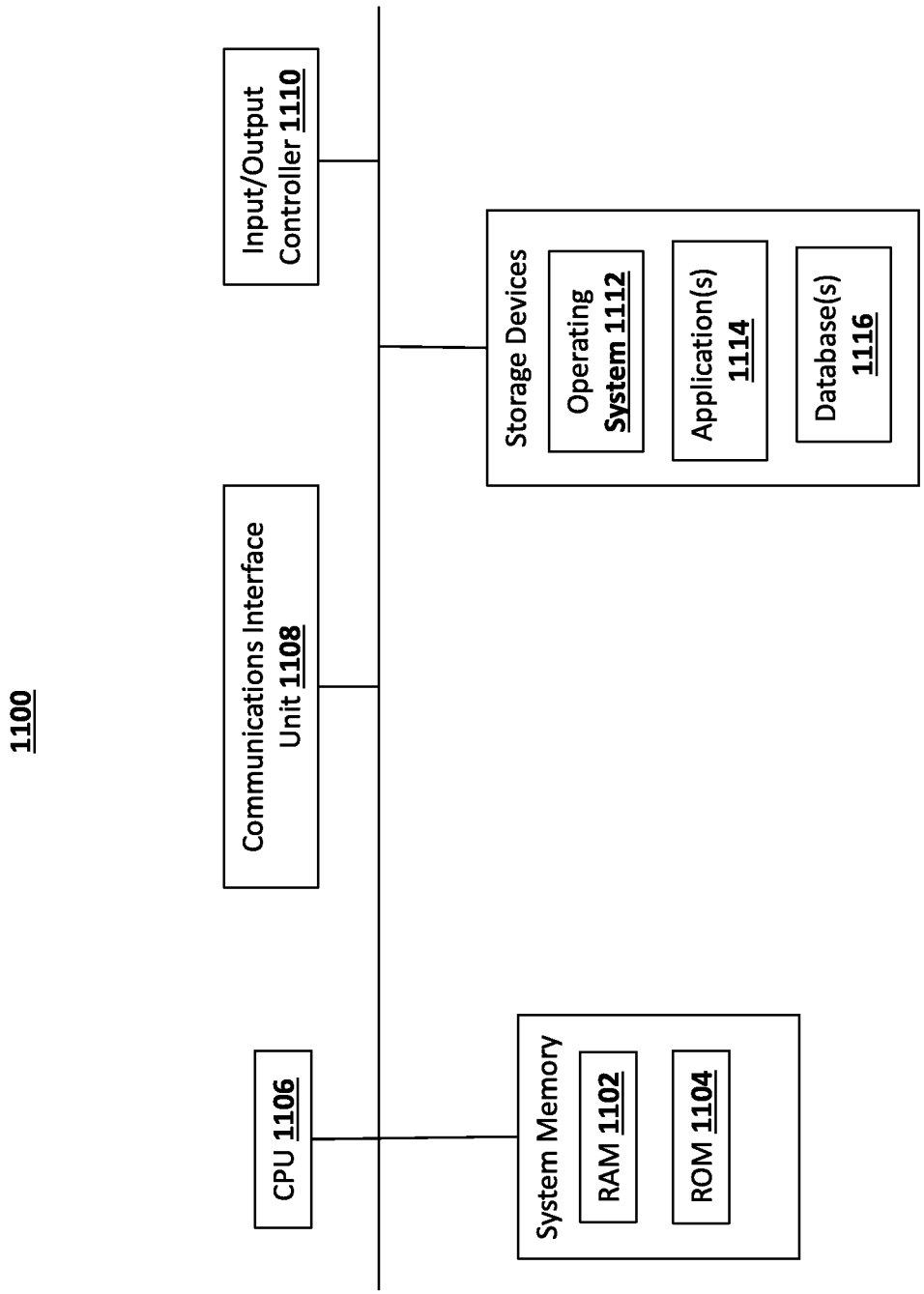
FIG. 11 is an exemplary computing device suitable for use with exemplary embodiments described herein.

The above-described steps may be performed in hardware logic, software logic, or a combination of hardware and software logic. FIG. 11 is a block diagram of a computing or electronic device, such as any of the components of the systems illustrated in FIGS. 1A-1B, and which are suitable for performing any of the processes described herein. Each of the components of these systems may be implemented on one or more computing devices 1100. In certain aspects, a plurality of the components of these systems may be included within one computing device 1100. In certain implementations, a component and a storage device may be implemented across several computing devices 1100.

The computing device 1100 comprises at least one communications interface unit, an input/output controller 1110, system memory, and one or more data storage devices. The system memory includes at least one random access memory (RAM) 1102 and at least one read-only memory (ROM) 1104. All of these elements are in communication with a central processing unit (CPU) 1106 to facilitate the operation of the computing device 1100. The computing device 1100 may be configured in many different ways. For example, the computing device 1100 may be a conventional standalone computer or alternatively, the functions of computing device 1100 may be distributed across multiple computer systems and architectures. In FIG. 11, the computing device 1100 is linked, via a network or a local network, to other servers or systems.

The computing device 1100 may be configured in a distributed architecture, wherein databases and processors are housed in separate units or locations. Some units perform primary processing functions and contain at a minimum a general controller or a processor and a system memory. In distributed architecture implementations, each of these units may be attached via the communications interface unit 1108 to a communications hub or port (not shown) that serves as a primary communication link with other servers, client or user computers and other related devices. The communications hub or port may have minimal processing capability itself, serving primarily as a communications router. A variety of communications protocols may be part of the system, including, but not limited to: Ethernet, SAP, SAS™, ATP, BLUETOOTH™, GSM and TCP/IP.

The CPU 1106 comprises a processor, such as one or more conventional microprocessors and if desired one or more supplementary co-processors such as math co-processors for offloading workload from the CPU 1106. The CPU 1106 is in communication with the communications interface unit 1108 and the input/output controller 1110, through which the CPU 1106 communicates with other devices such as other servers, user terminals, or devices. The communications interface unit 1108 and the input/output controller 1110 may include multiple communication channels for simultaneous communication with, for example, other processors, servers or client terminals.

The CPU 1106 is also in communication with the data storage device. The data storage device may comprise an appropriate combination of magnetic, optical or semiconductor memory, and may include, for example, RAM 1102, ROM 1104, flash drive, and an optical disc such as a compact disc or a hard disk or drive. The CPU 1106 and the data storage device each may be, for example, located entirely within a single computer or other computing device or connected to each other by a communication medium, such as a USB port, serial port cable, a coaxial cable, an Ethernet cable, a telephone line, a radio frequency transceiver or other similar wireless or wired medium or combination of the foregoing. For example, the CPU 1106 may be connected to the data storage device via the communications interface unit 808. The CPU 1106 may be configured to perform one or more particular processing functions.

The data storage device may store, for example, (i) an operating system 1112 for the computing device 1100; (ii) one or more applications 1114 (e.g., computer program code or a computer program product) adapted to direct the CPU 1106 in accordance with the systems and methods described here, and particularly in accordance with the processes described in detail with regard to the CPU 1106; or (iii) database(s) 1116 adapted to store information that may be utilized to store information required by the program.

The operating system 1112 and applications 1114 may be stored, for example, in a compressed, an uncompiled and/or an encrypted format, and may include computer program code. The instructions of the program may be read into a main memory of the processor from a computer-readable medium other than the data storage device, such as from the ROM 1104 or from the RAM 1102. While execution of sequences of instructions in the program causes the CPU 1106 to perform the process steps described herein, hard-wired circuitry may be used in place of, or in combination with, software instructions for implementation of the processes of the present disclosure. Thus, the systems and methods described are not limited to any specific combination of hardware and software.

Suitable computer program code may be provided for performing one or more functions in relation to aligning dietary behavior as described herein. The program also may include program elements such as an operating system 1112, a database management system and "device drivers" that allow the processor to interface with computer peripheral devices (e.g., a video display, a keyboard, a computer mouse, etc.) via the input/output controller 1110.

The term "computer-readable medium" as used herein refers to any non-transitory medium that provides or participates in providing instructions to the processor of the computing device 1100 (or any other processor of a device described herein) for execution. Such a medium may take many forms, including but not limited to, non-volatile media and volatile media. Non-volatile media include, for example, optical, magnetic, or opto-magnetic disks, or integrated circuit memory, such as flash memory. Volatile media include dynamic random access memory (DRAM), which typically constitutes the main memory. Common forms of computer-readable media include, for example, a floppy disk, a flexible disk, hard disk, magnetic tape, any other magnetic medium, a CD-ROM, DVD, any other optical medium, punch cards, paper tape, any other physical medium with patterns of holes, a RAM, a PROM, an EPROM or EEPROM (electronically erasable programmable read-only memory), a FLASH-EEPROM, any other memory chip or cartridge, or any other non-transitory medium from which a computer can read.

Various forms of computer readable media may be involved in carrying one or more sequences of one or more instructions to the CPU 1106 (or any other processor of a device described herein) for execution. For example, the instructions may initially be borne on a magnetic disk of a remote computer (not shown). The remote computer can load the instructions into its dynamic memory and send the instructions over an Ethernet connection, cable line, or even telephone line using a modem. A communications device local to a computing device 1100 (e.g., a server) can receive the data on the respective communications line and place the data on a system bus for the processor. The system bus carries the data to main memory, from which the processor retrieves and executes the instructions. The instructions received by main memory may optionally be stored in memory either before or after execution by the processor. In addition, instructions may be received via a communication port as electrical, electromagnetic or optical signals, which are exemplary forms of wireless communications or data streams that carry various types of information. The computer readable medium can be part of a computer device, with a processor that can process the medium.

All references cited herein, including patent applications and publications, are hereby incorporated by reference in their entirety. Various modifications of the disclosure, in addition to those described herein, will be apparent to those skilled in the art from the foregoing description. Such modifications are also intended to fall within the scope of the appended claims.

What is claimed is:

1. A method of treating a patient in need of treatment with eculizumab or an eculizumab variant and then monitoring the patient after administration of the eculizumab or the eculizumab variant has ceased, comprising:
    receiving a request from a prescriber to distribute a complement inhibitor;
    verifying that the prescriber has agreed to the following conditions to become a certified prescriber;
    (a) to vaccinate patients with a *Neisseria* meningococcal type B specific vaccine, and/or revaccinate patients according to a pre-determined schedule with a *Neisseria* meningococcal type B specific vaccine at predetermined times or intervals,
    (b) to provide the patients with educational materials regarding the complement inhibitor, and
    (c) that the prescriber has reviewed information relating to administering the complement inhibitor;
    accessing, using a computer with a processor programmed to perform the accessing, a database of the certified prescribers;
    adding, using the processor, the prescriber to the database of certified prescribers, the adding performed only if the prescriber has agreed to conditions (a)-(c) to become the certified prescriber in order to counsel the patient with regard to the risks associated with the complement inhibitor and is vaccinated or revaccinated to prevent a meningococcal infection, and that the prescriber is educated with regard to administering the complement inhibitor to the patient;
    receiving a requisition from the certified prescriber, the requisition requesting that the certified prescriber be provided with the complement inhibitor;
    inspecting, using the processor, the database of certified prescribers;
    authorizing, using the processor, the certified prescriber to receive the complement inhibitor only if the prescriber is in the database of certified prescribers;
    administering an effective amount of the eculizumab or the eculizumab variant to the patient who has been prescribing the eculizumab or the eculizumab variant by the certified prescriber,
    monitoring the patient during and after administration of the complement inhibitor for an adverse medical event including serious hemolysis, and if administration of the complement inhibitor to the patient has ceased and serious hemolysis occurs, then alerting the patient to seek treatment for the serious hemolysis, and treating the patient for the serious hemolysis.

2. The method of claim 1, wherein an entry in the database associated with the prescriber is associated with one or more flags certifying that the prescriber has agreed to comply with conditions (a)-(c); and the prescriber is only authorized to receive the eculizumab or an eculizumab variant if the one or more flags indicate that the prescriber has agreed to comply with conditions (a)-(c).

3. The method of claim 1, further comprising
    prompting, after a predetermined period of time, a reminder to follow up with the certified prescriber as to whether the certified prescriber is aware of the adverse event associated with providing the eculizumab or an eculizumab variant to the patient; and
    upon prompting, the computer comprises an interface and generates the alert to send to the prescriber.

4. The method of claim 1, further comprising monitoring for the serious hemolysis in PNH patients.

5. The method of claim 1, further comprising
    prompting, after a predetermined period of time, a reminder to provide the certified prescriber existing or updated educational materials about the eculizumab or an eculizumab variant; and
    an interface to send the reminder to the certified prescriber.

6. The method of claim 1, further comprising transmitting, after a predetermined period of time, a survey regarding the prescriber's compliance with one or more of conditions (a)-(c).

7. The method of claim 1, further comprising
    receiving a report from the certified prescriber that a patient was lost to follow up;
    identifying a new prescriber associated with the patient; and
    performing at least one of the following:
        verifying that the new prescriber is in the database of certified prescribers, or
        verifying that the patient is no longer being treated with the eculizumab or an eculizumab variant, and triggering a post-treatment reminder to follow up with the patient regarding the occurrence of the adverse event following discontinuation of the eculizumab or an eculizumab variant.

8. The method of claim 1, wherein the patient has been diagnosed with a complement-associated disorder.

9. The method of claim 8, wherein the patient has been diagnosed with paroxysmal nocturnal hemoglobinuria ("PNH"), atypical hemolytic uremic syndrome ("aHUS"), or Shiga-toxin-producing *E. coli* hemolytic uremic syndrome ("STEC-HUS").

10. The method of claim 8, wherein the patient has been diagnosed with a complement-associated disorder selected from the group consisting of age-related macular degeneration, graft rejection, bone marrow rejection, kidney graft rejection, skin graft rejection, heart graft rejection, lung graft rejection, liver graft rejection, rheumatoid arthritis, a pulmonary condition, ischemia-reperfusion injury, atypical hemolytic uremic syndrome, thrombotic thrombocytopenic purpura, paroxysmal nocturnal hemoglobinuria, dense deposit disease, age-related macular degeneration, spontaneous fetal loss, Pauci-immune vasculitis, epidermolysis bullosa, recurrent fetal loss, multiple sclerosis, traumatic brain injury, myasthenia gravis, cold agglutinin disease, dermatomyositis, Degos' disease, Graves' disease, Hashimoto's thyroiditis, type I diabetes, psoriasis, pemphigus, autoimmune hemolytic anemia, idiopathic thrombocytopenic purpura, Goodpasture syndrome, multifocal motor neuropathy, neuromyelitis optica, antiphospholipid syndrome, sepsis, hemorrhagic fever, and catastrophic antiphospholipid syndrome.

11. The method of claim 1, wherein the *Neisseria* meningococcal type B specific vaccine is multicomponent meningococcal serogroup B vaccine (4CMenB) or meningococcal group B vaccine (*Neisseria meningitidis* serogroup B recombinant lp2086 a05 protein variant antigen and *Neisseria meningitidis* serogroup B recombinant lp2086 b01 protein variant antigen).

* * * * *